US010005058B2

(12) United States Patent
Swager et al.

(10) Patent No.: US 10,005,058 B2
(45) Date of Patent: Jun. 26, 2018

(54) COMPOSITIONS AND METHODS FOR ARRANGING COLLOID PHASES

(71) Applicant: Massachusetts Institute of Technology, Cambridge, MA (US)

(72) Inventors: Timothy M. Swager, Newton, MA (US); Edmundo Daniel Blankschtein, Brookline, MA (US); Lauren Dell Zarzar, Cambridge, MA (US); Vishnu Sresht, Cambridge, MA (US); Ellen Sletten, Somerville, MA (US); Julia Ann Kalow, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days. days.

(21) Appl. No.: 14/929,131

(22) Filed: Oct. 30, 2015

(65) Prior Publication Data
US 2016/0151756 A1    Jun. 2, 2016

Related U.S. Application Data

(60) Provisional application No. 62/073,915, filed on Oct. 31, 2014.

(51) Int. Cl.
*B01J 13/00*    (2006.01)
*C12Q 1/40*    (2006.01)
(Continued)

(52) U.S. Cl.
CPC ............... *B01J 13/00* (2013.01); *C12Q 1/40* (2013.01); *C12Q 1/44* (2013.01); *B01F 5/0085* (2013.01);
(Continued)

(58) Field of Classification Search
CPC ...... B01F 2003/0834; B01F 2003/0842; B01F 5/0085; Y10T 428/2984; Y10T 428/2982; B01J 13/00; C12Q 1/40; C12Q 1/44
See application file for complete search history.

(56) References Cited

U.S. PATENT DOCUMENTS

| 4,870,026 A | 9/1989 | Wands et al. |
| 4,912,034 A | 3/1990 | Kalra et al. |

(Continued)

FOREIGN PATENT DOCUMENTS

| WO | WO 1992/17179 A1 | 10/1992 |
| WO | WO 1995/131500 A2 | 11/1995 |

(Continued)

OTHER PUBLICATIONS

International Search Report and Written Opinion for PCT/US2015/058268, dated Jan. 22, 2016.
(Continued)

*Primary Examiner* — Michael A Salvitti
(74) *Attorney, Agent, or Firm* — Wolf, Greenfield & Sacks, P.C.

(57) ABSTRACT

The present invention generally relates to colloids and methods for changing the arrangement of droplet phases. In some embodiments, the colloids and methods comprise a plurality of droplets comprising two or more components, such that the two or more components can change arrangement of the components in the presence of an external stimulus. In some embodiments, the change in component arrangement is reversible. In certain embodiments, the change in component arrangement forms Janus droplets.

22 Claims, 28 Drawing Sheets

(51) Int. Cl.
| | |
|---|---|
| C12Q 1/44 | (2006.01) |
| B01F 5/00 | (2006.01) |
| B01F 3/08 | (2006.01) |

(52) U.S. Cl.
CPC .............. B01F 2003/0834 (2013.01); B01F 2003/0842 (2013.01); Y10T 428/2982 (2015.01); Y10T 428/2984 (2015.01)

(56) References Cited

U.S. PATENT DOCUMENTS

| | | | |
|---|---|---|---|
| 5,332,661 | A | 7/1994 | Adamczyk et al. |
| 5,516,635 | A | 5/1996 | Ekins et al. |
| 6,180,418 | B1 | 1/2001 | Lee |
| 6,710,092 | B2 * | 3/2004 | Scher ............... A01N 25/28 504/363 |
| 7,067,590 | B2 | 6/2006 | Sato et al. |
| 7,625,951 | B2 | 12/2009 | Daunert et al. |
| 7,767,017 | B2 | 8/2010 | Lahann et al. |
| 7,947,772 | B2 | 5/2011 | Lahann et al. |
| 8,241,651 | B2 | 8/2012 | Lahann |
| 2002/0040065 | A1 * | 4/2002 | Scher ............... A01N 25/28 516/98 |
| 2004/0176479 | A1 * | 9/2004 | Scher ............... A01N 25/28 516/77 |
| 2006/0201390 | A1 | 9/2006 | Lahann et al. |
| 2007/0237800 | A1 | 10/2007 | Lahann et al. |
| 2008/0242774 | A1 | 10/2008 | Lahann et al. |
| 2009/0306311 | A1 * | 12/2009 | Reed ............... B01J 19/0033 526/59 |
| 2010/0062525 | A1 * | 3/2010 | Abbott ............... C09K 19/52 435/366 |
| 2011/0104777 | A1 | 5/2011 | Marquez et al. |
| 2012/0288852 | A1 | 11/2012 | Willson et al. |
| 2012/0319043 | A1 | 12/2012 | Stepien et al. |
| 2012/0328654 | A1 | 12/2012 | Huang et al. |
| 2014/0016177 | A1 | 1/2014 | Aizenberg et al. |
| 2014/0227684 | A1 * | 8/2014 | Hindson ............. C12Q 1/6876 435/6.1 |
| 2014/0350168 | A1 * | 11/2014 | Bormashenko ........ A61K 9/107 524/546 |
| 2015/0238636 | A1 | 8/2015 | Homyk et al. |
| 2016/0151753 | A1 | 6/2016 | Swager et al. |
| 2016/0151756 | A1 * | 6/2016 | Swager ............... B01J 13/00 435/19 |

FOREIGN PATENT DOCUMENTS

| | | |
|---|---|---|
| WO | WO 2009/061372 A1 | 5/2009 |
| WO | WO 2009/101113 A2 | 8/2009 |
| WO | WO 2015/051179 A1 | 4/2015 |
| WO | WO 2016/070027 A1 | 5/2016 |

OTHER PUBLICATIONS

International Search Report and Written Opinion for PCT/US2015/058286 dated Jan. 22, 2016.
Besnard et al., Multiple emulsions controlled by stimuli-responsive polymers. Adv Mater. May 28, 2013;25(20):2844-8. doi: 10.1002/adma.201204496. Epub Mar. 11, 2013.
McClements et al., Factors that affect the rate of oil exchange between oil-in-water emulsion droplets stabilized by a nonionic surfactant: Droplet size, surfactant concentration, and ionic strength. J. Phys. Chem. Jun. 1993; 97(28): 7304-08. doi: 10.1021/j100130a030.
Shah et al., Janus Supraparticles by Induced Phase Separation of Nanoparticles in Droplets. Adv. Mater. 2009; 21: 1949-1953. doi:10.1002/adma.200803115.
Tanaka et al., Dual stimuli-responsive "mushroom-like" Janus polymer particles as particulate surfactants. Langmuir. Jul. 20, 2010;26(14):11732-6. doi: 10.1021/la101237c.
Tu et al., One-step encapsulation and triggered release based on Janus particle-stabilized multiple emulsions. Chem Commun (Camb). Dec. 21, 2014;50(98):15549-52. doi: 10.1039/c4cc07854c. Epub Oct. 30, 2014.
Yusa et al., Fluorescence Studies of pH-Responsive Unimolecular Micelles Formed from Amphiphilic Polysulfonates Possessing Long-Chain Alkyl Carboxyl Pendants. Macromolecules. 2002; 35(27): 10182-88. doi: 10.1021/ma0212947. Epub Nov. 27, 2002.
International Preliminary Report on Patentability dated May 11, 2017 for Application No. PCT/US2015/058268.
International Preliminary Report on Patentability dated May 11, 2017 for Application No. PCT/US2015/058286.
Augustin et al., Nano- and micro-structured assemblies for encapsulation of food ingredients. Chem Soc Rev. Apr. 2009;38(4):902-12. doi: 10.1039/b801739p. Epub Dec. 4, 2008.
Bedford et al., Solubilities and volume changes attending mixing for the system: perfluoro-n-hexane-n-Hexane. J Am Chem Soc. 1958;80(2):282-5.
Brown et al., Stimuli-responsive surfactants. Soft Matter. 2013;9:2365-74.
Chakravarti et al., Liquid membrane multiple emulsion process of chromium (VI) separation from waste waters. Colloid Surface A. 1995;103:59-71.
Chen et al., Photoresponsive monodisperse cholesteric liquid crystalline microshells for tunable omnidirectional lasing enabled by a visible light-driven chiral molecular switch. Adv Opt Mater. 2014;2(9):845-48.
Chevallier et al., Photofoams: remote control of foam destabilization by exposure to light using an azobenzene surfactant. Langmuir. Feb. 7, 2012;28(5):2308-12. doi: 10.1021/la204200z. Epub Jan. 27, 2010.
Choi et al., Microfluidic design of complex emulsions. Chem Phys Chem. 2014;15:21-9.
Choi et al., One step formation of controllable complex emulsions: from functional particles to simultaneous encapsulation of hydrophilic and hydrophobic agents into desired position. Adv Mater. 2013;1-6.
Dominguez et al., Modeling and understanding the vapour-liquid and liquid-liquid interfacial properties for the binary mixture of n-heptane and perfluoro-n-hexane. J Mol Liq. 2013;185:36-43.
Engel et al, Insulin: intestinal absorption as water-in-oil-in-water emulsions. Nature. Aug. 24, 1968;219(5156):856-7.
Gao et al., Double emulsion templated microcapsules with single hollow cavities and thickness-controllable shells. Langmuir. Apr. 9, 2009;25(6):3832-8. doi: 10.1021/la804173b.
Gladysz et al., Structural, physical and chemical properties of fluorous compounds. Top Curr Chem. 2012;308:1-24.
Gresham et al., Use of a sustained-release multiple emulsion to extend the period of radio protection conferred by cysteamine. Nature. Nov. 19, 1971;234(5325):149-50.
Guzowski et al., The structure and stability of multiple microdroplets. Soft Matter. 2012;8: 7269-78.
Haase et al., Tailoring of high-order multiple emulsions by the liquid-liquid phase separation of ternary mixtures. Angew Chem Int Ed. 2014;53:1-6.
Kim et al., Fabrication of monodisperse gel shells and functional microgels in microfluidic devices. Angew Chem Int Ed. 2007;46:1819-22.
Kumar et al., Multiple Emulsions: A Review. Int J Rec Adv Pharm Rsch. Jan. 2012;2(1):9-19.
Lemal et al., Perspective on fluorocarbon chemistry. J Org Chem. Jan. 9, 2004;69(1):1-11.
Lone et al., Fabrication of polymeric janus particles by droplet microfluidics. RSC Advances. 2014;4:13322-33.
McClain et al., Interfacial roughness in a near-critical binary fluid mixture: X-ray reflectivity and near-specular diffuse scattering. Eur Phys J B. 1999;10:45-52.
Mukerjee et al., Adsorption of fluorocarbon and hydrocarbon surfactants to air-water, hexane-water, and perfluorohexane-water interfaces. Relative affinities and fluorocarbon-hydrocarbon nonideality effects. J Phys Chem. 1981;85:2298-303.
Nie et al., Janus and ternary particles generated by microfluidic synthesis: design, synthesis, and self-assembly. J Am Chem Soc. Jul. 26, 2006;128(29):9408-12.

(56) References Cited

OTHER PUBLICATIONS

Patravale et al., Novel cosmetic delivery systems: an application update. Int J Cosmet Sci. Feb. 2008;30(1):19-33. doi: 10.1111/j.1468-2494.2008.00416.x.

Riess, Overview of progress in the fluorocarbon approach to in vivo oxygen delivery. Biomater Artif Cells Immob Biotechnol. 1992;20(2-4):183-202.

Schutt et al., Injectable microbubbles as contrast agents for diagnostic ultrasound imaging: the key role of perfluorochemicals. Angew Chem Int Ed Engl. Jul. 21, 2003;42(28):3218-35.

Shah et al., Designer emulsions using microfluidics. Mat Today. Apr. 2008;11(4):18-27.

Shum et al., Droplet microfluidics for fabrication of non-spherical particles. Macromol Rapid Commun. Jan. 18, 2010;31(2):108-18. Doi: 10.1002/marc.200900590. Epub Nov. 24, 2009.

Song et al., Monodisperse w/w/w/ double emulsion induced by phase separation. Langmuir. 2012;28:12054-59.

Utada et al., Monodisperse double emulsions generated from a microcapillary device. Science. Apr. 22, 2005;308(5721):537-41.

Wong et al., Bioinspired self-repairing slippery surfaces with pressure-stable omniphobicity. Nature. Sep. 22, 2011;477(7365): 443-7.

Zhao et al., Microfluidic mass-transfer control for the simple formation of complex multiple emulsions. Angew Chem Int Ed. 2009;48:7208-11.

International Search Report and Written Opinion dated Nov. 30, 2017 for Application No. PCT/US2017/052209.

Alino et al., Liquid crystal droplets as a hosting and sensing platform for developing immunoassays. Langmuir. Aug. 2011;27:11784-9.

Han et al., Retroreflective Janus microparticle as a nonspectroscopic optical immunosensing probe. ACS Appl Mater Interfaces. May 4, 2016;8(17):10767-74.

Niu et al., Optical biosensor based on liquid crystal droplets for detection of cholic acid. Optics Commun. 2016;381:286-91.

Wu et al., Bioinspired nanocorals with decoupled cellular targeting and sensing functionality. Small. 2010;6(4):503-7.

Zhang et al., Janus emulsions for the detection of bacteria. ACS Central Sci. Apr. 26, 2017;3(4):309-13.

Berger et al., Stimuli-responsive bicomponent polymer Janus particles by "grafting from"/"grafting to" approaches. Macromolecules. 2008;41(24):9669-76. Epub Nov. 21, 2008.

Chen et al., Janus particles templated from double emulsion droplets generated using microfluidics. Langmuir. 2009;25(8):4320-3. Epub Mar. 18, 2009.

Choi et al., Patterned fluorescent particles as nanoprobes for the investigation of molecular interactions. Nano Letters. 2003;3(8):995-1000. Epub Jul. 11, 2003.

Kaufmann et al., "Sandwich" microcontact printing as a mild route towards monodisperse Janus particles with tailored bifunctionality. Adv Mater. 2011;23:79-83; Supporting Information pp. 1-8.

Kaufmann et al., Bifunctional Janus beads made by "sandwich" microcontract printing using click chemistry. J Mater Chem. 2012;22:6190-9. Epub Feb. 17, 2012.Electronic Suppl information pp. 1-9.

Li et al., Synthesis of biofunctional Janus particles. Macromol Rapid Comm. 2015;36:1200-4.

Nisisako et al., Synthesis of monodisperse bicolored Janus particles with electrical anisotropy using a microfluidic co-flow system. Adv Mater. 2006;18:1152-6.

Perro et al., Design and synthesis of Janus micro- and nanoparticles. J Mater Chem. 2005;15:3745-60. Epub Jul. 25, 2005.

Roh et al., Biphasic Janus particles with nanoscale anisotropy. Nat Mater. Oct. 2005;4:759-63. Epub Sep. 25, 2005.

\* cited by examiner

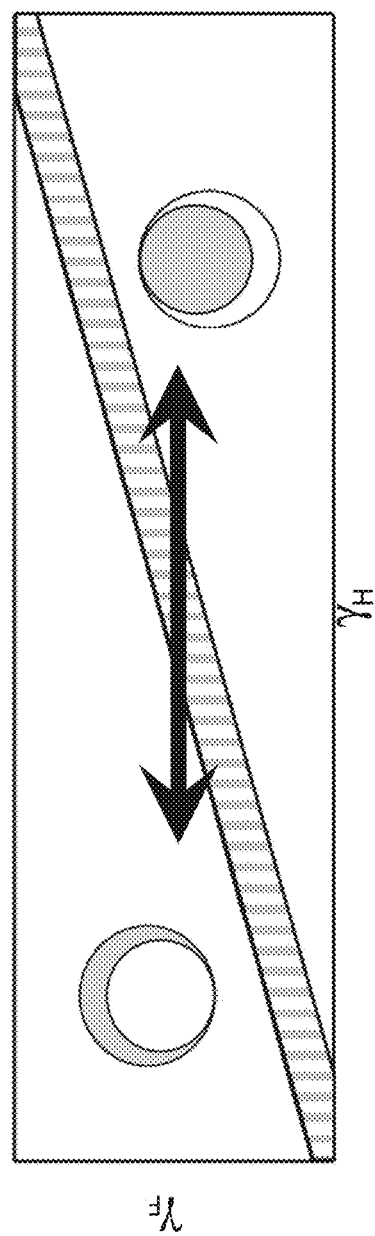

COMPOSITIONS AND METHODS FOR ARRANGING COLLOID PHASES

RELATED APPLICATIONS

This application claims priority under 35 U.S.C. § 119(e) to U.S. Provisional Application Ser. No. 62/073,915, filed Oct. 31, 2014, which is incorporated herein by reference in its entirety for all purposes.

FIELD OF THE INVENTION

The present invention generally relates to colloids and methods for arranging colloid phases.

BACKGROUND

Emulsification is a powerful age-old technique for mixing and dispersing immiscible inner phases within a continuous liquid phase. Consequently, emulsions are central components of medicine, food, and performance materials. Complex emulsions, including multiple emulsions and Janus droplets, are of increasing importance in pharmaceuticals and medical diagnostics, in the fabrication of microdroplets and capsules for food, in chemical separations, for cosmetics, and for performance materials like paints and coatings. As complex emulsion properties and functions are generally related to droplet geometry and composition, the development of rapid and facile fabrication approaches allowing precise control over the droplets' physical and chemical characteristics is critical. Significant advances in the fabrication of complex emulsions have been accomplished by a number of procedures, ranging from large-scale less precise techniques that give compositional heterogeneity using high-shear mixers and membranes to small-volume microfluidic methods. However, such approaches have yet to create droplet morphologies that can be controllably altered after emulsification.

SUMMARY OF THE INVENTION

The present invention provides colloids and methods for changing the arrangement of droplet phases.

In one aspect, methods for changing the arrangement of droplet phases is provided. In some embodiments, the method comprises providing a colloid comprising an outer phase, a plurality of droplets dispersed within the outer phase, wherein the plurality of droplets comprise two or more components, and stimulating the colloid, such that at least two of the two or more components change arrangement.

In another aspect, colloids are provided. In some embodiments, the colloid comprises an outer phase, a plurality of droplets dispersed within the outer phase, wherein the plurality of droplets comprise two or more components, wherein the two or more components have a first configuration, and wherein the two or more components have a second configuration in the presence of a stimulus.

Other advantages and novel features of the present invention will become apparent from the following detailed description of various non-limiting embodiments of the invention when considered in conjunction with the accompanying figures. In cases where the present specification and a document Incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

FIG. 7A is a schematic of how the interfacial tension variations in $\gamma_F$ and $\gamma_H$ induced by alterations in the effectiveness of a hydrocarbon surfactant translate into differences in drop morphology on a phase-stability diagram. Grey represents hexane, white represents perfluorohexane.

Figure 1A:
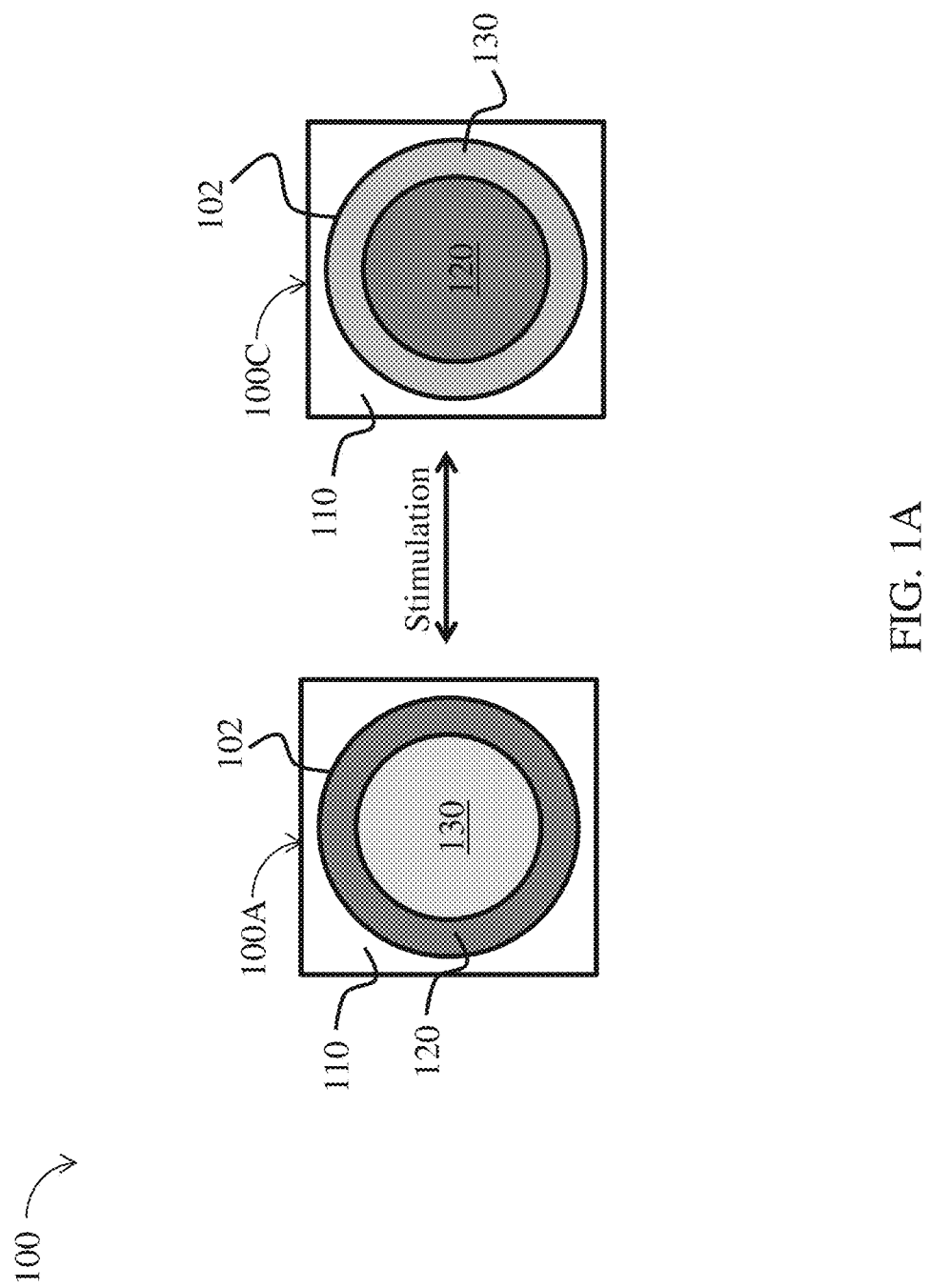
FIGS. 1A-D are schematic drawings illustrating changing the arrangement of colloid droplet phases, according to one set of embodiments.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

Embodiments described herein may be useful for arranging phases (e.g., in response to a stimulus) and/or components within a colloid. Complex droplets of controllable compositions and dynamic reconfigurable morphologies provide a new active element for novel and existing applications of emulsions and may be useful in numerous applications including food manufacturing, drug delivery, medical diagnostics, performance materials, cosmetics, MRI and ultrasound contrast agents, artificial blood, among other applications. The dynamic rearrangement of droplet phases and/or components can be broadly applied using a wide variety of chemicals, materials, and surfactants, as described herein. Droplets triggered by stimuli could be used, for example, to target release of drugs at tumors, to induce changes in color or transparency (e.g., for applications including color changing mediums and camouflage), as vehicles for sequestration of pollutants, as tunable lenses, as controlled release droplets in response to an stimulus, or as sensors. Emulsions with the characteristic ability to selectively "present" and "hide" specific liquid interfaces and controllably alter droplet morphology and symmetry may be useful for numerous applications and devices. Another advantageous feature provided by emulsions and methods described herein is the ability to readily incorporate additional compounds (e.g., magnetic nanoparticles, biological materials, polymers, metals, etc.) into various applications.

It should be understood that while the term colloid is used herein, those skilled in the art will understand that any colloid (e.g., a gel, an emulsion, a sol) comprising a plurality of droplets (e.g., a plurality of droplets dispersed in an outer phase) and/or a plurality of phases (e.g., a plurality of phases dispersed in an outer phase) may be used. Those skilled in the art will also be capable of selecting suitable materials and/or colloids for use in the embodiments described herein based on the teachings of the specification and examples below.

Colloids described herein offer numerous advantages to colloids known in the art, including the ability to reversibly, dynamically, and/or controllably change the arrangement and/or configuration of the components within the colloid (e.g., in response to an external stimulus, a change in temperature, or an analyte). In some embodiments, the colloid comprises an outer phase and a plurality of droplets (or regions) comprising two or more components. For example, in certain embodiments, the colloid comprises an outer phase and a plurality of droplets comprising a first component and a second component. In some cases, the colloid comprises an outer phase, and a plurality of droplets (or regions) comprising a first component, a second component, and a third component. Additional components are also possible.

In certain embodiments, the colloid comprises an outer phase and a plurality of droplets where a first component encapsulates a second component. In some embodiments, the colloid may be stimulated (e.g., by a first stimulus such as a change in temperature or exposure to an analyte) such that the components change arrangement and the second component encapsulates the first component. Those skilled in the art would understand that changes in arrangement as described herein do not refer to the motion of immiscible phases in a colloid due to regular fluid motion driven by passive diffusion and/or Brownian motion, but instead refer to the controlled change in arrangement of phases as a result of the addition of a particular stimulus or condition not present prior to the rearrangement of phases (or removal of a particular stimulus or condition, present prior to the rearrangement of phases), and are described in more detail below. In certain cases, a change in temperature may increase the passive diffusion and/or Brownian motion of phases present in the colloid but does not result in rearrangement of phases as described herein (e.g., until the temperature reaches a critical temperature as described in more detail below).

In some embodiments, the outer phase and at least one component are substantially immiscible. In certain embodiments, the outer phase and at least two components are substantially immiscible Immiscible, as used herein, refers to two components (or a phase and a component) having an interfacial tension of greater than or equal to 0.01 mN/m as determined by an inverted pendant drop goniometer. Conversely, miscible, as used herein, refers to two components (or a phase and a component) having an interfacial tension of less than 0.01 mN/m as determined by an inverted pendant drop goniometer.

Referring to FIG. 1A, in some embodiments, colloid 100 comprises an outer phase 110, and a plurality of droplets (shown as exemplary droplet 102) comprising a first component 120 and a second component 130 at least partially encapsulated by the first component (configuration 100A). In certain embodiments, colloid 100 having configuration 100A may be stimulated (e.g., by a first stimulus) such that at least a portion of the plurality of droplets obtain a second configuration 100C, such that second component 130 at least partially encapsulates first component 120. That is to say, in certain embodiments, the first component and the second component may transpose. In some embodiments, the rearrangement between the first configuration and the second configuration may be reversible. For example, in some cases, colloid 100 comprising a plurality of droplets having second configuration 100C may be stimulated (e.g., by a second stimulus) such that at least a portion of the plurality of droplets return to first configuration 100A.

Figure 1B:
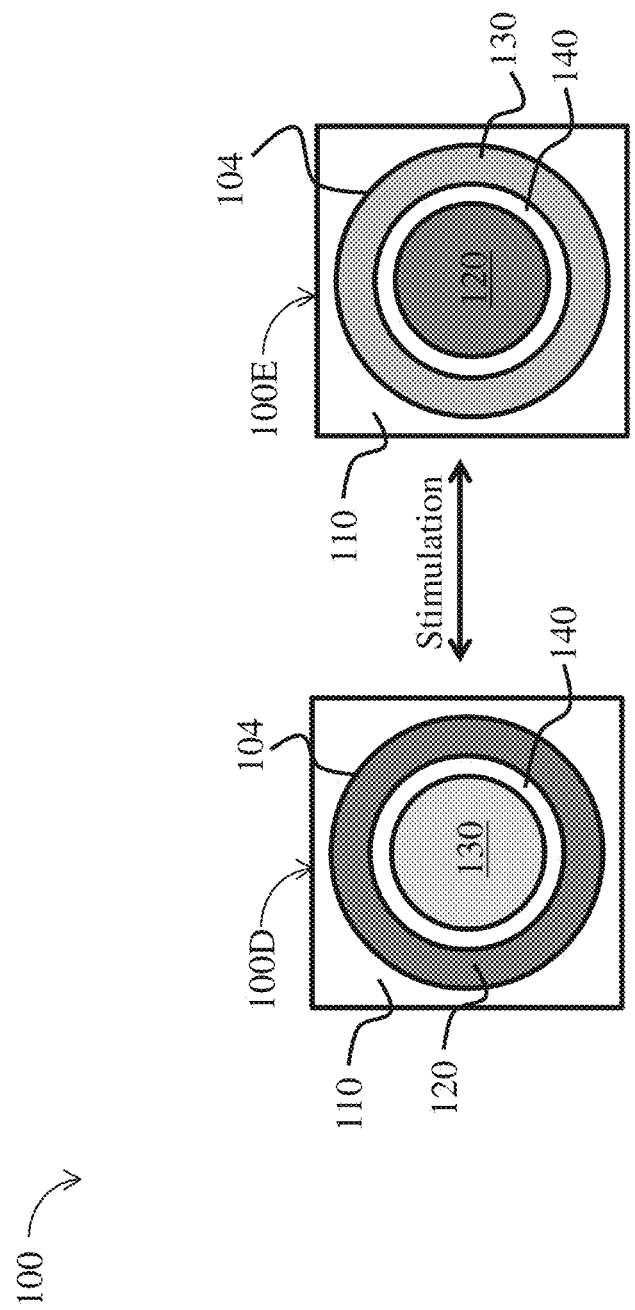

In some embodiments, the colloid comprises a plurality of droplets comprising three or more components. In some such embodiments, the colloid may be stimulated such that two or more of the three of more components change arrangement. In an exemplary embodiment, a colloid comprises a plurality of droplets comprising a first component at least partially encapsulating a second component, the second component at least partially encapsulating a third component, and upon stimulation, the first component changes arrangements with the second and/or third components. For example, as illustrated in FIG. 1B, colloid 100 may comprise outer phase 110 and a plurality of droplets (shown as exemplary droplet 104) comprising a first component 120, a second component 130, and a third component 140. In certain embodiments, the third component at least partially encapsulates the second component, and the first component at least partially encapsulates the second and third components. In certain embodiments, colloid 100 having configuration 100D may be stimulated (e.g., by a first stimulus) such that at least a portion of the plurality of droplets obtain a second configuration 100E, such that the second component at least partially encapsulates the first and third components. In some embodiments, the rearrangement between configuration 100D and 100E are reversible. For example, in some cases, colloid 100 comprising a plurality of droplets having configuration 100E may be stimulated (e.g., by a second stimulus) such that at least a portion of the plurality of droplets return to configuration 100D.

In certain embodiments, the colloid may be stimulated such that two or more components become miscible. Referring now to FIG. 1D, in some embodiments, the colloid comprises outer phase 110, and a plurality of droplets (shown as exemplary droplet 108) comprising a first component 120 and a second component 130 at least partially encapsulated by the first component (configuration 100A). In certain embodiments, colloid 100 having configuration 100A may be stimulated (e.g., by a first stimulus) such that at least a portion of the plurality of droplets obtain a second configuration 100F, such that the first component and the second component form a miscible mixture 125. Those skilled in the art would understand that droplets comprising two or more, three or more, or four or more components may, upon stimulation, have two or more, three or more, or four or more components form a miscible mixture.

In some cases, the colloid may comprises two or more miscible components that, upon stimulation, become immiscible. Referring again to FIG. 1D, in certain embodiments, the colloid having a plurality of droplets comprising mixture 125 such that (configuration 100F), upon stimulation, the mixture separates into first component 120 and second component 130, at least partially encapsulated by first component 120 (configuration 100A).

While exemplary configurations for a plurality of droplets having two or more components, are described above, those skilled in the art would understand based upon the teaching of this specification that additional reconfigurations and rearrangements are also possible (e.g., the third component encapsulating the first and second components, etc.). Those skilled in the art would also understand, based upon the teachings of this specification, that droplets comprising four or more, five or more, or six or more components are also possible and that such droplets may also be stimulated such that two or more of the components rearrange.

Those skilled in the art will understand that while much of the specification refers to a plurality of droplets, the colloid may comprises an outer phase and a plurality of regions comprising two or more components, such that the two or more components change configuration (e.g., after stimulation).

In some cases, the methods and colloids described herein may be useful for the formation of Janus droplets. For example, in certain embodiments, the first component and second component may change configuration upon stimulation such that neither component encapsulates the other component in the new configuration. In some such embodiments, the colloid may comprise a plurality of Janus droplets. In some such embodiments, the colloid is stimulated such that the plurality of droplets form Janus droplets.

Figure 1C:
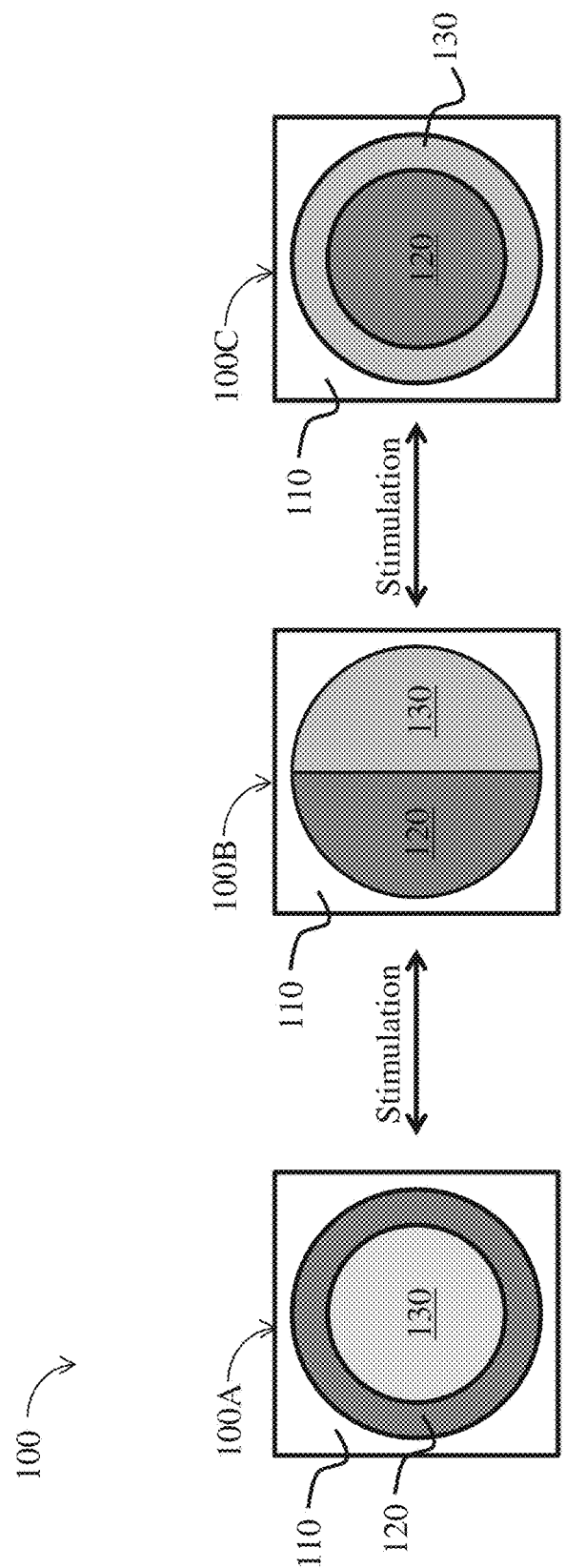
Figure 1D:
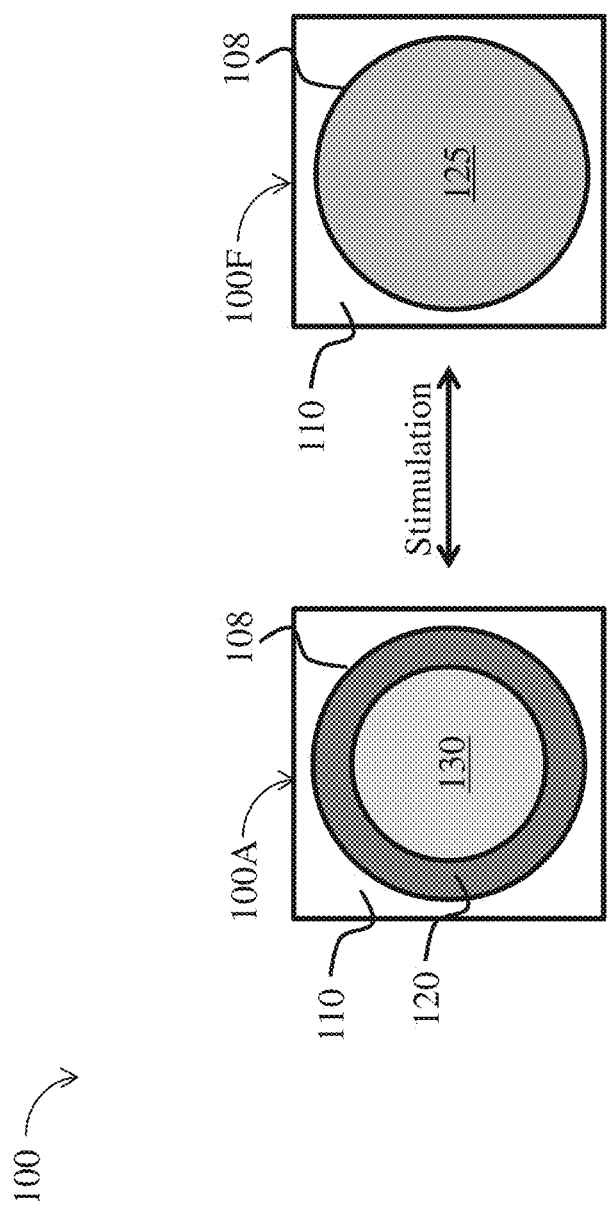

For example, as shown in FIG. 1C, second configuration 100B may comprise a Janus droplet. That is to say, in certain embodiments, the two or more components do not encapsulate each other but interface with the outer phase to form Janus droplets. Janus droplets are generally known in the art and comprise droplets wherein the droplet is divided into two distinct parts comprising two different components. For example, in some embodiments, the emulsion comprises an outer phase and a plurality of droplets comprising a first component and a second component, wherein the plurality of droplets are Janus droplets.

In some embodiments, colloid 100 may, upon stimulation, change configuration from first configuration 100A, to an intermediate configuration 100B. In some cases, colloid 100 may reversibly return (upon a second stimulation) to first configuration 100A, or obtain third configuration 100C. In certain embodiments, the change in configuration between configuration 100A and configuration 100B, or between configuration 100C and configuration 100B, is reversible. That is to say, in some embodiments, colloid 100 may change arrangement from the second configuration and/or the third configuration to the first configuration in the presence of a second stimulus, different than a first stimulus.

The first stimulus and the second stimulus may be the same type of stimulus (e.g., light, heat, force, an analyte, an acid) but differ in a property of the stimulus (e.g., different intensities of light, different magnitudes of temperature change, different magnitudes of force, different analytes, different analyte concentrations). In an exemplary embodiments, the first stimulus may be an analyte present at a first concentration, and the second stimulus comprises the analyte present in a second concentration, less than the first concentration (e.g., the degradation of an analyte below a particular concentration results stimulates the colloid).

In some cases, the first stimulus and the second stimulus may be different (e.g., a different type of stimulus, a different property of the stimulus).

An exemplary screening test for determining suitable stimuli includes preparing a colloid having a plurality of droplets comprising a first component and a second component at least partially encapsulated by the first component. The second component further comprises a dye (miscible in the outer phase but not present in the outer phase), dispersed within the second component, the dye being immiscible and not dispersed within the first component. Upon adding or exposing the colloid to the stimulus, as described herein, the first component and second component rearrange such that the second component at least partially encapsulates the first component and the dye is observed in the outer phase.

The colloid may be stimulated for any suitable amount of time. For example, in some cases, the stimulus is added to the colloid and not removed. In certain embodiments, the stimulus is applied for a specific amount of time. In some such embodiments, the stimulus may be applied for between about 1 second and about 10 seconds, between about 5 seconds and about 60 seconds, between about 30 seconds and about 2 minutes, between about 1 minute and about 5 minutes, between about 2 minutes and about 10 minutes, between about 5 minutes and about 15 minutes, between about 10 minutes and about 30 minutes, between about 15 minutes and about 60 minutes, between about 30 minutes and about 2 hours, between about 1 hour and about 6 hours, or between about 2 hours and about 24 hours. In some cases, the colloid may be stimulated for greater than 24 hours.

In certain embodiments, the second stimulus is the removal of the first stimulus. That is to say, in some embodiments, the two or more components in the plurality of droplets have a first configuration and change arrangement in the presence of a first stimulus to a second configuration. In some such embodiments, the two or more components may return to the first configuration upon removal of the first stimulus. Stimuli are described in more detail, below. The term component, as used herein, generally refers to a portion of a droplet comprising a group of substantially similar molecules, a group of substantially similar compounds, and/or a phase (e.g., a non-aqueous phase, an aqueous phase) comprising such molecules and/or compounds. Those skilled in the art would understand that the term component is not intended to refer to a single molecule or atom. In some embodiments, the component is a liquid phase (e.g., a gas phase, an aqueous phase, non-aqueous phase) comprising a group of substantially similar compounds and/or molecules. For example, in some cases, each component may occupy at least about 1 vol %, at least about 2 vol %, at least about 5 vol %, at least about 10 vol %, at least about 20 vol %, at least about 50 vol %, at least about 70 vol %, at least about 90 vol %, at least about 95 vol %, or at least about 99 vol % of the total volume of the two or more components present within each droplet.

In some embodiments, the plurality of droplets comprise two or more components (e.g., three or more components, four or more components, five or more components) such that at least two of the two or more components change configuration in the presence of a stimulus. In some cases, the two or more components may be substantially miscible over a range of temperatures (e.g., below a critical temperature of the two or more components, above a critical temperature of the two or more components). In some cases, the two or more components may also be substantially immiscible over a different range of temperatures (e.g., above the critical temperature of the two or more components, below the critical temperature of the two or more components) than the range of temperatures over which they are miscible.

In some embodiments, the plurality of droplets comprise two or more components, wherein the two or more components are immiscible below or above a critical temperature of the two or more components. In some embodiments, the critical temperature is an upper consolute temperature of the two or more components. In some such embodiments, the two components are substantially miscible above the upper consolute temperature of the two or more components and substantially immiscible below the upper consolute temperature of the two or more components. In some embodiments, the critical temperature is a lower consolute temperature of the two or more components. That is to say, in some such embodiments, the two components are substantially miscible below the lower consolute temperature of the two or more components and substantially immiscible above the lower consolute temperature of the two or more components. In some embodiments, the miscibility of the two or more components is reversible. That is to say, the miscibility of the two or more components can be changed, in some embodiments, by increasing or decreasing the temperature to a temperature greater than, or less than, the critical temperature.

In some embodiments, two or more components may comprises two components having an upper consolute temperature greater than or equal to about 0° C., greater than or equal to about 5° C., greater than or equal to about 8° C., greater than or equal to about 10° C., greater than or equal to about 15° C., greater than or equal to about 18° C., greater than or equal to about 20° C., greater than or equal to about 22° C., greater than or equal to about 25° C., greater than or equal to about 27° C., greater than or equal to about 30° C., greater than or equal to about 35° C., greater than or equal to about 40° C., greater than or equal to about 50° C., greater than or equal to about 55° C., or greater than or equal to about 60° C. In certain embodiments, the upper consolute temperature of two components present in the two or more components is less than about 70° C., less than about 60° C., less than about 55° C., less than about 50° C., less than about 40° C., less than about 35° C., less than about 30° C., less than about 27° C., less than about 25° C., less than about 22° C., less than about 20° C., less than about 18° C., less than about 15° C., less than about 10° C., less than about 8° C., or less than about 5° C. Combinations of the above-referenced ranges are also possible (e.g., an upper consolute temperature of greater than or equal to about 0° C. and less than about 70° C.). Other ranges are also possible. Those skilled in the art would be capable of selecting suitable methods for determining the upper consolute temperature of two or more components.

In some embodiments, two or more components may comprises two components having a lower consolute temperature greater than or equal to about 0° C., greater than or equal to about 5° C., greater than or equal to about 8° C., greater than or equal to about 10° C., greater than or equal to about 15° C., greater than or equal to about 18° C., greater than or equal to about 20° C., greater than or equal to about 22° C., greater than or equal to about 25° C., greater than or equal to about 27° C., greater than or equal to about 30° C., greater than or equal to about 35° C., greater than or equal to about 40° C., greater than or equal to about 50° C., greater than or equal to about 55° C., or greater than or equal to about 60° C. In certain embodiments, the lower consolute temperature of two components present in the two or more components is less than about 70° C., less than about 60° C., less than about 55° C., less than about 50° C., less than about 40° C., less than about 35° C., less than about 30° C., less than about 27° C., less than about 25° C., less than about 22° C., less than about 20° C., less than about 18° C., less than about 15° C., less than about 10° C., less than about 8° C., or less than about 5° C. Combinations of the above-referenced ranges are also possible (e.g., a lower consolute temperature of greater than or equal to about 0° C. and less than about 70° C.). Other ranges are also possible. Those skilled in the art would be capable of selecting suitable methods for determining the lower consolute temperature of two or more components.

In some embodiments, the two or more components may be selected such that the interfacial tension between the two or more components allows for slight changes in interfacial tension (e.g., in response to a stimulus that changes the conformation and/or a property of the one or more components) to change the configuration of the two or more components within at least a portion of the plurality of droplets. The morphology of the plurality of droplets is generally controlled by interfacial tension between two or more components within the droplets. For example, a complex emulsion of any immiscible liquids F and H (at a given volume ratio) in a third immiscible liquid W has interfacial tensions of the H-W interface, $\gamma_H$, the F-W interface, $\gamma_F$, and the F-H interface, $\gamma_{FH}$. In some cases, $\gamma_F$ and $\gamma_H$ may be greater than $\gamma_{FH}$ such that combinations of liquids H and F have low interfacial tension just below a critical temperature of the two liquids. Generally, such multi-phase droplets may have equilibrium spherical shapes and may exhibit, for example, thermodynamically-permissible internal configurations including (1) liquid H completely engulfs liquid F (FIG. 2A), (2) liquids H and F form a Janus droplet (FIG. 2B), and (3) liquid F completely engulfs liquid H (FIG. 2C). These droplet configurations may be characterized, in some cases, by two contact angles, $\theta_H$ between the H-W and F-H interfaces, and $\theta_F$ between the F-H and F-W interfaces. The three interfacial tensions acting along the interfaces must be in equilibrium for the droplet configuration to be stable as can be expressed by the following equations:

$$\cos\theta_H = \frac{\gamma_F^2 - \gamma_H^2 - \gamma_{FH}^2}{2\gamma_{FH}\gamma_H}$$

$$\cos\theta_F = \frac{\gamma_H^2 - \gamma_F^2 - \gamma_{FH}^2}{2\gamma_{FH}\gamma_F}$$

In some cases, $\theta_H$ approaches 0 and $\theta_F$ approaches 0, yielding the following two relationships:

$$\theta_H = 0 \Rightarrow \gamma_F = \gamma_H + \gamma_{FH}$$

$$\theta_F = 0 \Rightarrow \gamma_H = \gamma_F + \gamma_{FH}$$

Figure 2A:
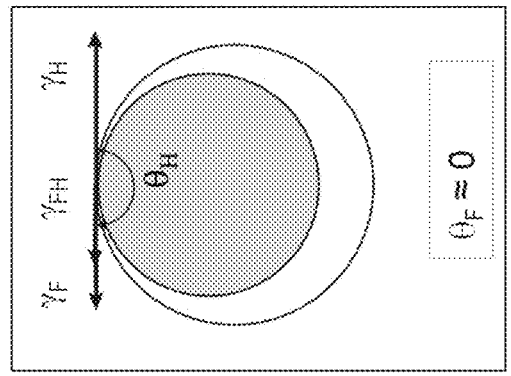
FIG. 2A is a schematic of the effect of interfacial tensions on the configuration of a complex droplet where encapsulation of a fluorocarbon (F) by a hydrocarbon (H) in water (W) is favored, according to one set of embodiments.
Figure 2B:
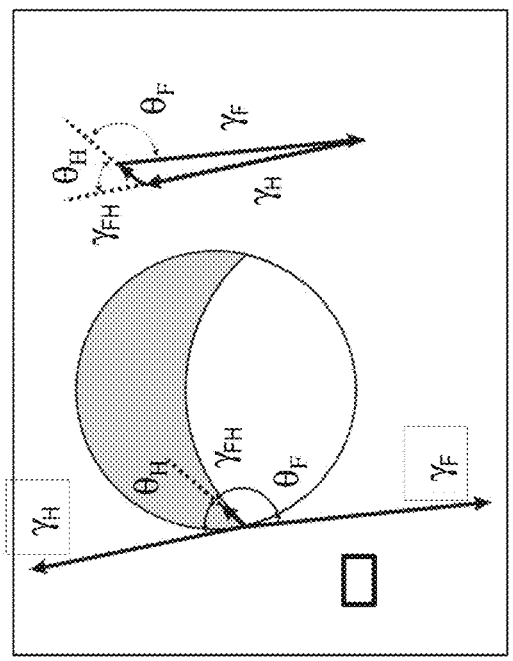
FIG. 2B is a schematic of the effect of interfacial tensions on the configuration of a complex droplet where the formation of a Janus droplet of a fluorocarbon (F) and a hydrocarbon (H) in water (W) is favored, according to one set of embodiments.
Figure 2C:
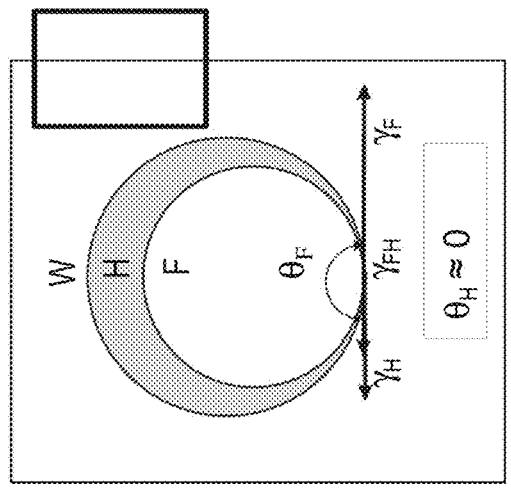
FIG. 2C is a schematic of the effect of interfacial tensions on the configuration of a complex droplet where encapsulation of a hydrocarbon (H) by a fluorocarbon (F) in water (W) is favored, according to one set of embodiments.

These equations generally indicate that when $\gamma_F - \gamma_H \geq \gamma_{FH}$, the droplets can rearrange to configuration (1) in FIG. 2A. Conversely, when $\gamma_H - \gamma_F \geq \gamma_{FH}$, the droplets can rearrange to configuration (3) in FIG. 2C. However, when the difference between $\gamma_H$ and $\gamma_F$ is on the order of $\gamma_{FH}$, the droplets can rearrange to a Janus droplet geometry associated with configuration (2) in FIG. 2B. As such, slight changes in the balance of $\gamma_H$ and $\gamma_F$ may induce changes in the droplet's morphology. In some embodiments, the two or more components may be selected such that changes in the balance of $\gamma_H$ and $\gamma_F$ result in the reversible change of configuration of the two or more components within a portion of the plurality of droplets.

In certain embodiments, each component is different and a fluid. In some cases, one or more components may be a gas. In some embodiments, one or more components may be a liquid.

In some embodiments, at least one of the two or more components comprises a hydrocarbon (e.g., a hydrocarbon fluid). Non-limiting examples of suitable hydrocarbons include alkanes (e.g., hexane, heptane, decane, dodecane, hexadecane), alkenes, alkynes, aromatics (e.g., benzene, toluene, xylene, benzyl benzoate, diethyl phalate), oils (e.g., natural oils and oil mixtures including vegetable oil, mineral oil, and olive oil), liquid monomers and/or polymers (e.g., hexanediol diacrylate, butanediol diacrylate, polyethylene glycols, trimethylolpropane ethoxylate triacrylate), alcohols (e.g., butanol, octanol, pentanol, ethanol, isopropanol), ethers (e.g., diethyl ether, diethylene glycol, dimethyl ether), dimethyl formamide, acetonitrile, nitromethane, halogenated liquids (e.g., chloroform, dichlorobenzene, methylene chloride, carbon tetrachloride) brominated liquids, iodinated liquids, lactates (e.g., ethyl lactate), acids (e.g., citric acid, acetic acid), trimethylamine, liquid crystal hydrocarbons (e.g., 5-cyanobiphenyl), combinations thereof, and derivatives thereof, optionally substituted. In some embodiments, the hydrocarbon comprises a halogen group, sulfur, nitrogen, phosphorous, oxygen, or the like. Other hydrocarbons or organic chemicals are also possible. In some embodiments, the outer phase comprises a hydrocarbon.

In some embodiments, at least one of the two or more components comprises a fluorocarbon (e.g., a fluorocarbon fluid). Non-limiting examples of suitable fluorocarbons include fluorinated compounds such as perfluoroalkanes (e.g., perfluorohexanes, perfluorooctane, perfluorodecalin, perfluoromethylcyclohexane), perfluoroalkenes (e.g., perfluorobenzene), perfluoroalkynes, and branched fluorocarbons (e.g., perfluorotributylamine). Additional non-limiting examples of suitable fluorocarbons include partially fluorinated compounds such as methoxyperfluorobutane, ethyl nonafluorobutyl ether, 2H,3H-perfluoropentane, trifluorotoluene, perfluoroiododide, fluorinated or partially fluorinated oligomers, 2,2,3,3,4,4,5,5,6,6,7,7,8,8,9,9-hexadecafluorodecane-1,10-diylbis(2-methylacrylate), perfluoroiodide, and 2-(trifluoromethyl)-3-ethoxydodecafluorohexane. Other fluorocarbons are also possible. In some embodiments, the outer phase comprises a fluorocarbon.

In some embodiments, at least one of the two or more components comprises a silicone such as silicone oil. Non-limiting examples of suitable silicone oils include polydimethylsiloxane and cyclosiloxane fluids. In some embodiments, the outer phase comprises a silicone.

In some embodiments, at least one of the two or more components comprises water. In some embodiments, at least one of the two or more components comprises an ionic liquid (e.g., an electrolyte, a liquid salt). Non-limiting examples of ionic liquids include 1-allyl-3-methylimidazolium bromide, 1-allyl-3-methylimidazolium chloride, 1-benzyl-3-methylimidazolium hexafluorophosphate, 1-butyl-1-methylpyrrolidinium hexafluorophosphate. Other ionic liquids are also possible. In some embodiments, the outer phase comprises water.

In certain embodiments, at least one of the two or more components comprises a deuterated compound (e.g., a deuterated hydrocarbon, a deuterated fluorocarbon). Colloids having components comprising deuterated compounds may be useful in various applications including, for example, NMR and MRI.

In some embodiments, at least one of the two or more components comprises a polymer (e.g., polyethylene glycol). In certain embodiments, the polymer is a block copolymer. In certain embodiments, the polymer is a liquid crystal polymer (e.g., a thermotropic liquid crystal polymer). In certain embodiments, the polymer is a biopolymer (e.g., gelatin, alginate).

In some embodiments, at least one of the two or more components comprises a liquid crystal. Non limiting examples of liquid crystals include thermotropic liquid crystals (e.g. 4-Cyano-4'-pentylbiphenyl), lyotropic liquid crystals, and metallotropic liquid crystals (e.g. $ZnCl_2$).

In some embodiments, at least one of the two or more components comprises a gas.

Non-limiting examples of combinations of components present in the plurality of droplets described herein include hexane and perfluorohexane, carbon tetrachloride and perfluorohexane, chloroform and perfluorohexane, hexane and perfluorodecalin, hexane and perfluoromethylcyclohexane, hexane and perfluorotributylamine, isopropanol and hexadecane, ethyl lactate and heptane, acetic acid and decane, and triethylamine and water. Other combinations and materials are also possible.

In some embodiments, at least one of the two or more components comprises a combination of the materials described above (e.g., comprising a hydrocarbon, a fluorocarbon, a silicone, or combinations thereof). In some embodiments, a first component may comprise at least two miscible compounds (e.g., or two compounds at a temperature at which the compounds are miscible), both or all of which may be immiscible with a second component (e.g., the first component comprises a mixture of hydrocarbons and the second component comprises a fluorocarbon).

In some embodiments, one or more components and/or the outer phase comprises an additional compound dispersed in the one or more components and/or the outer phase. In certain embodiments, the additional compound is dispersible in a first component and not dispersible in a second component. In some cases, at least a portion of the additional compound is dispersible in the first component and not dispersible in the second component (e.g., a surfactant). In some embodiments, the additional compound may be dispersible or not dispersible in the outer phase. Non-limiting examples of suitable additional compounds include particles (e.g., magnetic particles/nanoparticles, silica particles), biological molecules (e.g., insulin), pharmaceutical compounds, polymers, surfactants, cells, bacteria, viruses, active pharmaceutical ingredients, and metals or metal particles. Other additional compounds are also possible and those skilled in the art would be capable of selecting such compounds based upon the teachings of this specification.

Those skilled in the art would be capable of selecting suitable components such that the components have a first configuration (i.e. arrangement) in the absence of a stimulus and a second configuration (i.e. arrangement) in the presence of the stimulus. In some embodiments, the components have a first configuration (i.e. arrangement) in the presence of a first stimulus and a second configuration (i.e. arrangement) in the presence of a second stimulus.

The outer phase may comprise any suitable material. In some embodiments, the outer phase is a solid. In certain embodiments, the outer phase is a liquid. In some embodiments, the outer phase is a gel. Generally, the two or more components comprising the plurality of droplets may be substantially immiscible with the outer phase. In some embodiments, the outer phase is an aqueous phase (e.g., comprising water, a hydrocarbon, a fluorocarbon). In certain embodiments, the outer phase is a non-aqueous phase (e.g., comprising a silicone, comprising a polymer). In some embodiments, the non-aqueous phase comprises a hydrocarbon, a fluorocarbon, a silicone, or the like, as described above in the context of the two or more components, and is substantially immiscible with at least one of the two or more components. The use of an non-aqueous outer phase may be advantageous in certain applications including, but not limited to, sensing in low humidity environments. For example, a plurality of droplets comprising fluorocarbon/hydrocarbon phases can be created in a liquid silicone matrix. The silicone can be crosslinked of polymerized to change its mechanical properties. In some embodiments, at least a portion of the droplets may be deformed and/or aligned by mechanically deforming (e.g., applying a mechanical force to) the outer phase. Advantageously, non-aqueous materials such as silicone can generally absorb and transport organic molecules, which may also be useful in sensing applications.

Those skilled in the art would be capable, based upon the teachings of the specification and the examples below, of selecting suitable materials for use as an outer phase based upon the miscibility of those materials (e.g., such that the two or more components may be substantially immiscible with the outer phase). In some embodiments, the colloid comprises a plurality of droplets dispersed in the outer phase wherein the outer phase is a liquid (e.g., a liquid polymer, a gel precursor) and is solidified (e.g., polymerized) or gelled (e.g., crosslinked). Those skilled in the art would be capable of selecting suitable methods for solidifying or gelling the outer phase.

In certain embodiments, a colloid comprising a plurality of droplets having two or more components may be formed. In some such embodiments, the colloid may be stimulated such that the two or more components rearrange (e.g., forming a new configuration, forming Janus droplets). After stimulating, the outer phase may be solidified (e.g., polymerized, gelled, or the like) such that the rearrangement of components is maintained. In certain embodiments, the plurality of droplets may be stimulated after solidification of the outer phase such that two or more components in at least a portion of the plurality of droplets rearrange configuration.

In some embodiments, the colloid further comprises an additional compound such as an amphiphilic compound. In certain embodiments, the amphiphilic compound is miscible in the outer phase. In some embodiments, the amphiphilic compound is miscible in at least one of the two or more components. In certain embodiments, the amphiphilic compound has a greater miscibility in at least one of the two or more components than a miscibility in the outer phase. In some embodiments, the amphiphilic compound is dispersed at the interface between the outer phase and the plurality of droplets. In certain embodiments, the amphiphilic compound is dispersed at the interface between at least two of the two or more components. The amphiphilic compound may preferentially interact with one or more components or the outer phase. Those skilled in the art would be capable of selecting a suitable amphiphilic compound based upon the teachings of the specification and examples below. Miscibility may be determined, for example, as described above using an inverted pendant drop goniometer.

In some embodiments, the amphiphilic compound is a surfactant. Non-limiting examples of suitable surfactants include fluorosurfactants (e.g., commercially available fluorosurfactants such as Zonyl® or Capstone®), anionic surfactants (e.g., sodium dodecyl sulfate (SDS)), cationic surfactants (e.g., alkyltrimethyl ammonium chloride, alkylmethyl ammonium bromide), non-ionic surfactants (e.g., alkyl poly(ethylene oxide)), zwitterionic surfactants (e.g., alkyl betain, $C_8$-lecitin), polymeric surfactants, gemini surfactants, particulate surfactants (e.g., graphene oxide, silica particles), and combinations thereof. Other surfactants are also possible.

In some embodiments, the amphiphilic compound is a nucleic acid (e.g., DNA, RNA). In certain embodiments the amphiphilic compound comprises an amino acid (e.g., a peptide, a protein). In some embodiments, the amphiphilic compound comprises a biomaterial. Non-limiting examples of suitable biomaterials include carbohydrates or derivatives thereof, saccharides or derivatives thereof (e.g., sialic acid), lipids or derivatives thereof, enzymes, chromophores or the like. Those skilled in the art would be capable of selecting suitable biomaterials based upon the teachings of the specification and the examples below.

In some embodiments, the amphiphilic compound comprises a perfluorinated segment. In some embodiments, the amphiphilic compound comprises ethylene glycol.

In some embodiments, the amphiphilic compound is capable of forming metal complexes.

In certain embodiments, the amphiphilic compound is graphene oxide.

In some embodiments, the amphiphilic compound may be a particle (e.g., a silica particle, a polymer particle, a Janus particle, a nanoparticle, a gel particle).

In some embodiments, the amphiphilic compound is added to a colloid (e.g., a colloid comprising an outer phase and a plurality of droplets comprising two or more components, dispersed within the outer phase). In some such embodiments, the amphiphilic compound may act as a stimulus (e.g., stimulating the colloid such that the two or more components change configuration (i.e. arrangement)).

The term stimulating as used herein generally refers to the addition, removal, or change of a condition, a compound, or the environment (e.g., temperature, pressure, pH) such that the interfacial tension between two or more components is changed. Those skilled in the art will be capable of selecting suitable stimulus for use with the colloid described herein based upon the teachings of the specification and will understand stimulation does not comprise substantially removing a component and/or replacing the entirety of a component with a new component. However, in some embodiments, stimulating the colloid may result in a component, additional compound, and/or surfactant present in the colloid changing molecular conformation such that the component, additional compound, and/or amphiphilic compound is chemically distinguishable after stimulation (e.g., an acid cleavable component, additional compound, and/or amphiphilic compound that cleaves in the presence of an acid, a photosensitive component, additional compound, and/or amphiphilic compound that changes conformation or molecular structure after exposure to light) as compared to before stimulation. In certain embodiments, stimulating the colloid may result in a change in interfacial tension between two or more components such that the two or more component rearrange and/or mix.

In some embodiments, stimulating the colloid changes the arrangement of the colloid, as described herein. For example, in certain embodiments, stimulating the colloid changes the molecular conformation of at least one of the two or more components. In certain embodiments, stimulating the colloid releases at least one of the two or more components, additional compounds, and/or amphiphilic compounds, from a portion of the plurality of droplets. In some embodiments, stimulating the colloid changes an average birefringence of the colloid (e.g., increases the birefringence, decreases the birefringence). In certain embodiments, stimulating the colloid changes the color of the colloid and/or changes an average optical transmission of the colloid. In some cases, stimulating the colloid may change an average luminesce of the colloid. In certain embodiments, stimulating the colloid may change an average density of the colloid.

Those skilled in the art would understand that changing a property of a colloid refers to a property of the colloid immediately before that differs in a substantially measurable way from the property of the colloid at some relatively short time (e.g., seconds, minutes, hours) after stimulation. Those skilled in the art would also be capable of selecting methods for determining the change in the property of the colloid (e.g., measuring the average birefringence, measuring the optical transmission, measuring the density, etc.) based upon the specification and examples below.

In some embodiments, stimulating the colloid comprises exposing the colloid to an external stimulus (e.g., such that the configuration of two or more components is changed). In some such embodiments, the external stimulus comprises electromagnetic radiation, ionizing radiation, a magnetic field, an electric field, a mechanical force (e.g., pressure, direct contact), or combinations thereof. Those skilled in the art would be capable of selecting suitable components and methods of applying such external stimuli based upon the teachings of the specification and examples below. For example, in some such embodiments, at least one of the two or more components may comprise a magnetic particle such that, in the presence of a magnetic field, the at least one of the two or more components transposes or changes configuration with at least one additional component of the two or more components.

Figure 7B:
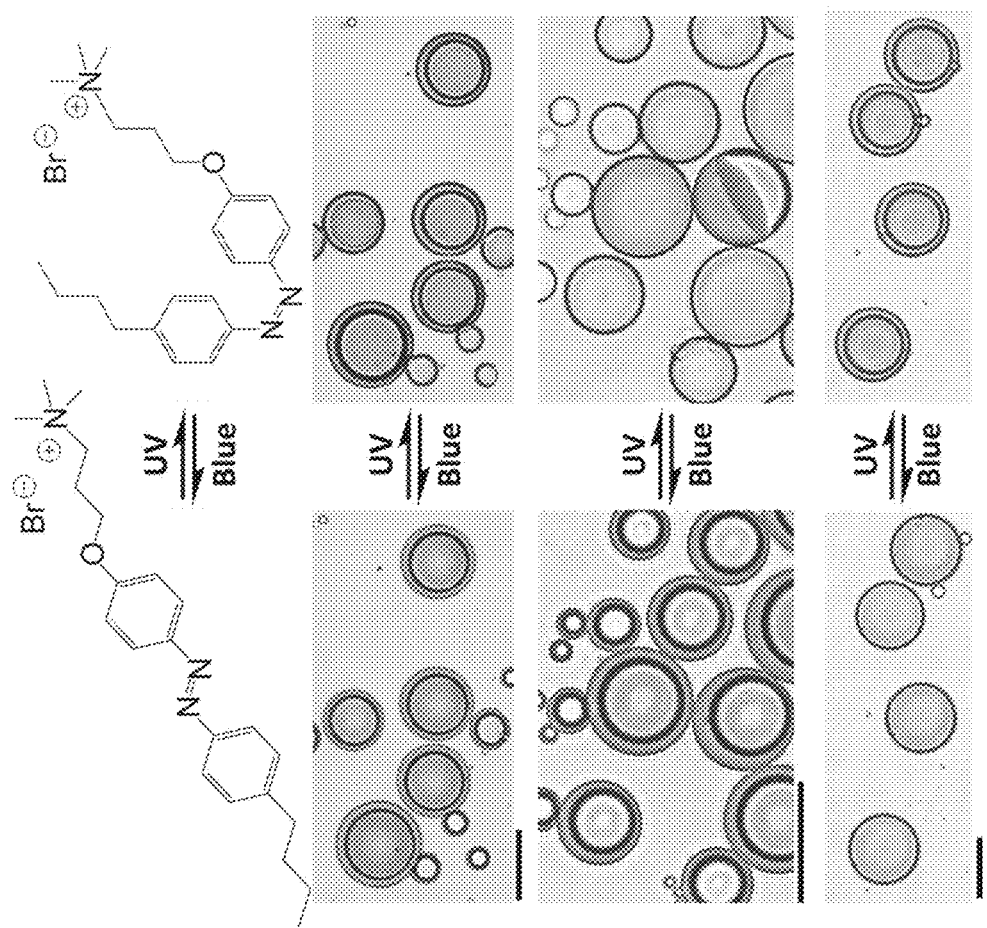
FIG. 7B shows a chemical structure of the light-responsive surfactant which reversibly isomerizes under UV and blue light between the trans form of the surfactant (left) and the less effective cis form (right). Below are optical micrographs of hexane-perfluorohexane emulsions that are tuned to undergo specific morphological transitions in response to light. Hexane is dyed, and the aqueous phase consists of Zonyl and the light-responsive surfactant at top. Top: droplets undergo complete inversion. Middle: F/H/W double emulsion droplets transition to Janus droplets. Most droplets are viewed from the top, but one is lying on its side allowing a view of the droplet profile. Bottom: Janus droplets transition to a H/F/W double emulsion.

In certain embodiments, the external stimulus comprises photochemical stimulation (e.g., exposing the colloid to light). The light may comprise any suitable wavelength, including but not limited to radio waves (e.g., a wavelength between about 1 cm and about 100 m), infrared light (e.g., a wavelength between about 700 nm and about 1 cm), visible light (e.g., a wavelength between about 400 nm and about 700 nm), ultraviolet (UV) light (e.g., a wavelength between about 10 nm and about 400 nm), and x-rays (e.g., a wavelength between about 0.01 nm and about 10 nm). For example, in some embodiments, at least one of the two or more components comprises a light-sensitive surfactant (e.g., azobenzene) such that the light-sensitive surfactant reversibly changes molecular confirmation in the presence of UV light and/or visible blue light, causing the at least one component to transpose or change configuration with at least one additional component (FIG. 7B).

In some embodiments, stimulating the colloid comprises changing the temperature of the colloid (e.g., such that the configuration of two or more components is changed). In certain embodiments, changing the temperature of the colloid comprises heating the colloid. In some embodiments, changing the temperature of the colloid comprises cooling the colloid. In some embodiments, the colloid is at a first temperature, below a critical upper consolute temperature of two or more components, and the temperature is increased to a second temperature above the critical upper consolute temperature of the two or more components such that two or more of the two or more components change configuration. Those skilled in the art would be capable of selecting suitable methods of heating or cooling the colloid based upon the teaching of the specification and examples below.

In certain embodiments, stimulating the colloid comprises applying a force and/or pressure to the colloid such that the configuration of two or more components is changed.

In some embodiments, stimulating the colloid comprises adjusting the ionic strength and/or adjusting the pH of the colloid. For example, in some embodiments, adjusting the pH of the colloid comprises adding an acid (e.g., HCl) or a base (e.g., NaOH). For example, in some such embodiments, at least one of the two or more components comprises a pH-sensitive surfactant (e.g., N-dodecylpropane-1,3-diamine) and/or an acid-cleavable surfactant (e.g., sodium 2,2-bis(hexyloxy)propyl sulfate) such that the pH-sensitive surfactant and/or the acid-cleavable surfactant changes charge and/or cleaves in the presence of an acid or a base, causing the at least one component to transpose or change configuration with at least one additional component.

In certain embodiments, stimulating the colloid comprises adding an analyte to the colloid. The analyte may comprise any suitable material (e.g., a vapor analyte, a liquid analyte, a solid analyte) such that the incorporation of the analyte into a portion of the plurality of droplets or the outer phase causes the two or more components to change configuration. Those skilled in the art would be capable of selecting analytes and components suitable for colloid based upon the teaching of the specification and the examples below. Non-limiting examples of suitable analytes includes a biological compound, a drug, a macromolecule, a salt, an electrolyte, an enzyme, a nucleic acid, a carbohydrate, a peptide, a protein, a lipid, a phosphate, a sulfonate, a virus, a pathogen, an oxidant, a reductant, a toxin, a chemical warfare agent, an explosive, carbon dioxide, a surfactant, or combinations thereof. Components can be selected such that two or more components have a first interfacial tension in the absence of an analyte, and a second interfacial tension in the presence of the analyte such that the configuration of the two or more components is different in the presence of the analyte than in the absence of the analyte.

In an exemplary embodiment, an enzyme may be added to the colloid comprising a plurality of droplets such that the enzyme interacts with one or more of the components, additional compounds, and/or amphiphilic compounds present in the plurality of droplets. In some such embodiments, the enzyme may interact with the component, additional compound, and/or amphiphilic compound (e.g., such as a surfactant which cleaved in the presence of the enzyme) such that the two or more components change configuration, as described herein.

In another exemplary embodiment, one or more components may comprise an additional compound such as a surfactant that is capable of interacting with a biological analyte. Non-limiting examples of biological analytes include glucose, cholesterol, triglycerides, and bilirubin. In some such embodiments, the colloid may reversibly change arrangement of two or more components in the presence of a biological analyte such that the change in arrangement can be detected (e.g., by optical transmission). In certain embodiments, the colloid changes arrangement at a particular critical concentration of the biological analyte.

In some embodiments, stimulating the colloid causes a chemical transformation of one or more components present in the colloid such that two or more components change configuration. Non-limiting examples of chemical transformations which may result in two or more components changing configuration include enzymatic degradation, enzymatic synthesis, ionization, cleavage, coupling, hybridization, aggregation, hydrolysis, isomerization, reduction, oxidation, and host-guest interactions of one or more components (or component materials such as a surfactant). Other chemical transformations are also possible. In some embodiments, a portion of the plurality of droplets can be solidified (e.g., polymerized) such that a first configuration, a second configuration different than the first configuration, and/or a Janus droplet configuration solid droplets can be fabricated. Those skilled in the art will be capable of selecting appropriate materials for solidifying droplets and may include, in some embodiments, adding a crosslinker (e.g., a fluorinated acrylate) to the colloid such that the crosslinker crosslinks at least one of the two or more components, wherein the at least one of the two or more components comprises a crosslinkable polymer. In certain embodiments, solidifying droplets comprises adding a gelling agent (e.g., calcium-crosslinked alginate, gelatin, agar, or the like). In some embodiments, solidifying droplets comprises drying the droplets. In certain embodiments, solidifying droplets comprises changing the temperature such that one or more components solidify (e.g., a component comprising a liquid crystal or liquid crystal polymer that solidifies below the new temperature, a component comprising a liquid with a relatively high freezing point such that changing the temperature solidifies the liquid). Other methods of solidifying droplets are also possible and are known in the art.

Colloids described herein may be formed using any suitable method. For example, in some embodiments, an outer phase material, a first component, and a second component are mixed and emulsified, forming an outer phase and a plurality of droplets in the outer phase having a first component and a second component at least partially encapsulated by the first component. Suitable methods for emulsifying the fluid are known in the art and may comprise sonication, high shear mixing, shaking, passing the fluid through a membrane, or injecting the two or more components into the outer phase through a small diameter channel.

In certain embodiments, the outer phase material, the first component, and the second component may be mixed at a temperature at which the first component material and the second component material are miscible. In some such embodiments, the temperature of the mixture may be changed (e.g., increased, decreased) to a temperature such that the first component and the second component are immiscible and form a plurality of droplets in the outer phase having a first component and a second component at least partially encapsulated by the first component. While much of the description herein applies to two components, those skilled in the art would understand that such methods may be useful for the formation of colloids comprising a plurality of droplets having three or more, four or more, or five or more components.

The colloids described herein may be useful in a number of applications. In an exemplary embodiment, the colloids described herein may be used for sensing of an analyte. For example, in some such embodiments, two or more phases in the colloid may change arrangement in the presence of an analyte such that the change in arrangement can be detected (e.g., by a change in optical transmission, birefringence, etc. of the colloid). In another exemplary embodiment, the colloids described herein may be used as tunable lenses. In certain embodiments, measurements of the optical properties (e.g., transmission, absorption, reflection, focal distance, and scattering) of either individual droplets or of the bulk colloid can be indicative of specific droplet arrangements. For example, when a change in droplet arrangement is correlated with an analyte of interest (i.e., enzyme, pollutant, virus, etc.), then, the colloids can be used as sensors in which an optical measurement serves as a readout mechanism of the presence of the analyte. In certain embodiments, for systems in which there is a change in an analyte of interest over time (e.g., progress of a chemical reaction, such as degradation of a chemical by an enzyme over time), tracking of the changes in optical properties of the colloid over time can be used to, for example, analyze reaction rates or analyte concentrations. In some such embodiments, the arrangement of the components of the colloid changes in the presence of a stimulus such that the colloid obtains a transparent state over a particular range of time.

In yet another exemplary embodiment, the colloids described herein may be used for release of a macromolecule such as an active pharmaceutical ingredient or biomolecule (e.g., insulin). For example, in some such embodiments, the colloid comprising a plurality of droplets having two or more components may comprises an active pharmaceutical ingredient or biomolecule miscible and present within one of the components at least partially encapsulated by another component. In the presence of an analyte (e.g., glucose), two or more components may change arrangement such that the component containing the active pharmaceutical ingredient or biomolecule at least partially encapsulates the remaining components and the active pharmaceutical ingredient or biomolecule is released into the outer phase.

As used herein, the term "active pharmaceutical ingredient" (also referred to as a "drug") refers to an agent that is administered to a subject to treat a disease, disorder, or other clinically recognized condition, or for prophylactic purposes, and has a clinically significant effect on the body of the subject to treat and/or prevent the disease, disorder, or condition. Active pharmaceutical ingredients include, without limitation, agents listed in the United States Pharmacopeia (USP), Goodman and Gilman's The Pharmacological Basis of Therapeutics, 10th edition, McGraw Hill, 2001; Katzung, B. (editor), Basic and Clinical Pharmacology, McGraw-Hill/Appleton & Lange, 8th edition (Sep. 21, 2000); Physician's Desk Reference (Thomson Publishing); and/or The Merck Manual of Diagnosis and Therapy, 17th edition (1999), or the 18th edition (2006) following its publication, Mark H. Beers and Robert Berkow (editors), Merck Publishing Group, or, in the case of animals, The Merck Veterinary Manual, 9th edition, Kahn, C. A. (ed.), Merck Publishing Group, 2005. Preferably, though not necessarily, the active pharmaceutical ingredient is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention. In certain embodiments, the active pharmaceutical ingredient is a small molecule. Exemplary active pharmaceutical ingredients include, but are not limited to, anti-cancer agents, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, prostaglandins, etc.

As used herein, a "fluid" is given its ordinary meaning, i.e., a liquid or a gas. A fluid cannot maintain a defined shape and will flow during an observable time frame to fill the container in which it is put. Thus, the fluid may have any suitable viscosity that permits flow. If two or more fluids are present, each fluid may be independently selected among essentially any fluids (liquids, gases, and the like) by those of ordinary skill in the art.

EXAMPLES

The following examples illustrate embodiments of certain aspects of the invention. It should be understood that the methods and/or materials described herein may be modified and/or scaled, as known to those of ordinary skill in the art.

Example 1

The following example describes the general formation of an emulsion. For example, hydrocarbon and fluorocarbon liquids were heated until miscible and emulsified. The temperature required varied depending on the solutions. Solutions were emulsified either in bulk by shaking or by coaxial glass capillary microfluidics and cooled to induce phase separation. For example, for hexane-perfluorohexane emulsions, the emulsions were chilled on ice prior to imaging and often imaged while immersed in a cool water bath to maintain a temperature below 20° C. For microfluidics, syringe pumps were used to inject the outer phase and component using a glass capillary microfluidic device made from an outer square capillary and component cylindrical capillary pulled to a 30 µm tip using a Micropipette Puller (Sutter Instrument Company). The microfluidic setup was heated above the $T_c$ of the component solution using a heat lamp. Emulsions were then cooled below $T_c$ to induce phase separation. Emulsions were observed to be stable during the time periods used (e.g., on the order days).

Example 2

The following example describes the formation of an emulsion. According to the methods described in Example 1.

Figure 3:
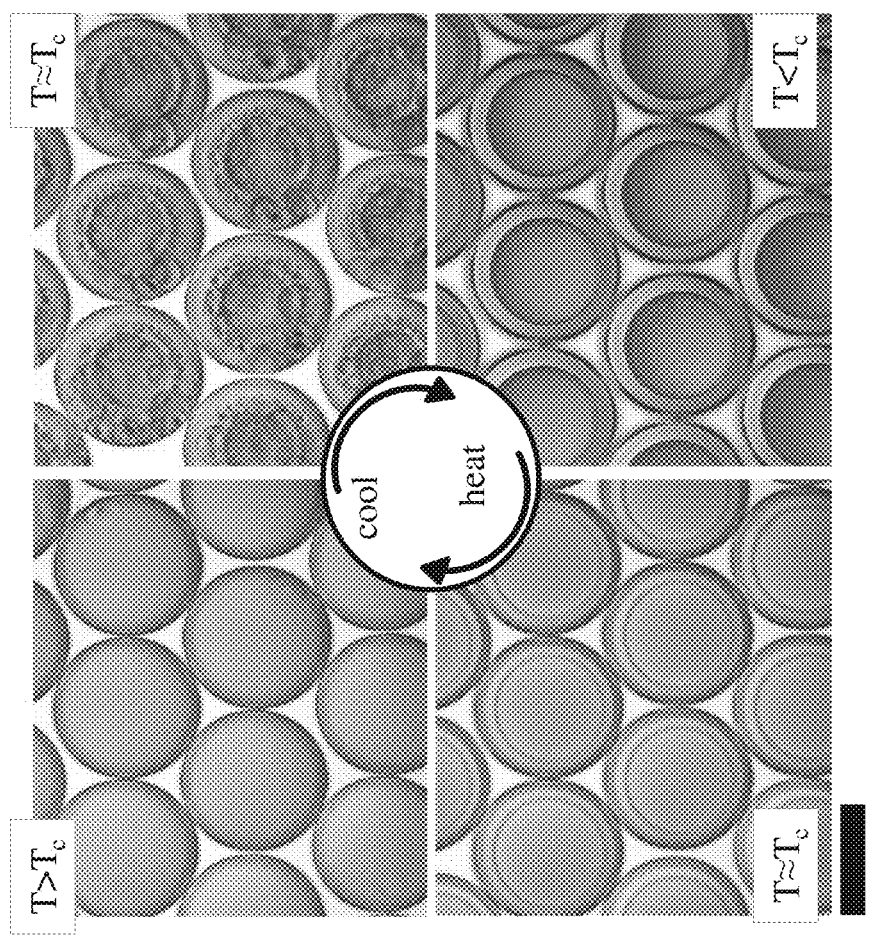
FIG. 3 shows optical micrographs of the formation of complex emulsions comprising hexane and perfluorohexane, according to certain embodiments.
Figure 4A:
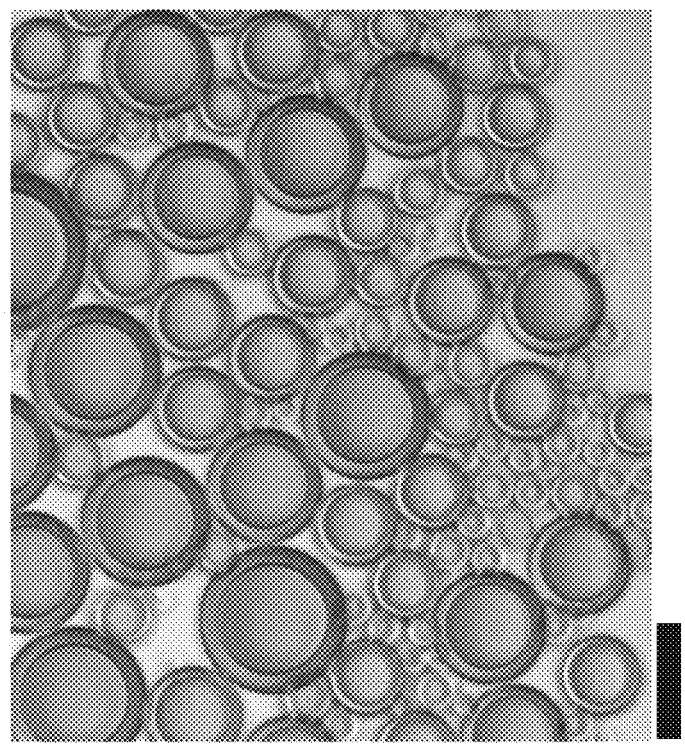
FIG. 4A shows optical micrographs of a complex emulsion comprising hexane and perfluorohexane, according to one set of embodiments.
Figure 4B:
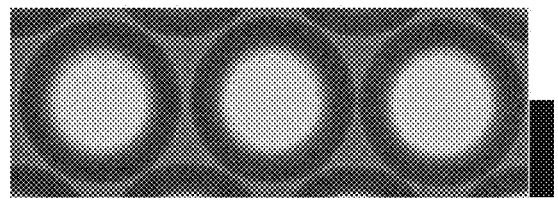
FIG. 4B shows a confocal micrograph of a complex emulsion comprising hexane and perfluorohexane, according to one set of embodiments.

Fluorocarbons are generally lipophobic as well as hydrophobic and many fluorocarbon and hydrocarbon liquids are immiscible at room temperature but have a low upper consolute temperature ($T_c$) and mix with gentle heating. Hexane and perfluorohexane, for example, have a $T_c$ of 22.65° C. A 1:1 volume ratio of hexane and perfluorohexane was mixed and emulsified above $T_c$ in an aqueous solution of Zonyl FS-300 fluorosurfactant (FIG. 3, top left). Cooling below $T_c$ induced phase separation and yielded structured complex droplets (FIG. 2. Bottom right). Above $T_c$, hexane and perfluorohexane are miscible and emulsified in 0.1% Zonyl (FIG. 3, top left). Below $T_c$, hexane and perfluorohexane phase separate to create a hexane-in-perfluorohexane-in-water (H/F/W) double emulsion (FIG. 3, bottom right). This phase separation was reversible. These complex emulsions were readily produced in bulk by shaking warm hexane-perfluorohexane liquid in a surfactant solution (FIG. 4A). Although these droplets were polydisperse, the morphology and composition of the droplets was highly uniform. Chemical partitioning during phase separation gave directed compartmentalization of solutes (FIG. 4B), forming hexane/perfluorohexane/water double emulsion droplets in a microfluidic device. Temperature-induced phase separation of liquids may provide a facile, scalable approach to fabrication of complex functional emulsions.

Example 3

The following example describes changing the arrangement of phases of an emulsion. The emulsion was formed as in Example 2.

Figure 5:
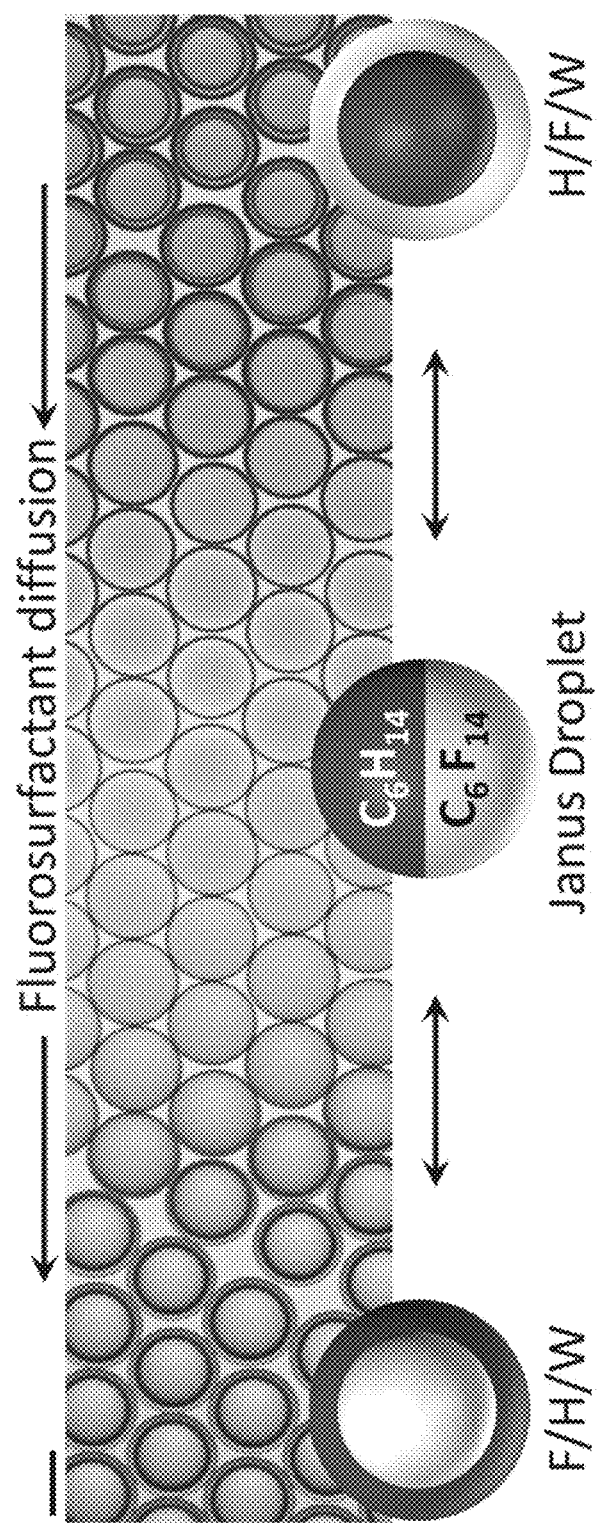
FIG. 5 is an optical micrograph of hexane-perfluorohexane droplets reconfigured in response to variation in the concentration of Zonyl fluorosurfactant as it diffuses through 0.1% SDS (sodium dodecyl sulfate).

A 1:1 volume mixture of hexane and perfluorohexane in 0.1% Zonyl® FS-300 (Zonyl, a nonionic fluorosurfactant) generated hexane-in-perfluorohexane-in-water (H/F/W) double emulsions indicating a decrease in perfluorohexane interfacial tension, $\gamma_F$. In comparison, emulsification of the same hexane-perfluorohexane mixture in water containing 0.1% sodium dodecyl sulfate (SDS, an anionic hydrocarbon surfactant), yielded F/H/W double emulsions as a result of decreased hexane interfacial tension, $\gamma_H$. A small volume of 10% Zonyl was introduced to F/H/W droplets in 0.1% SDS, and the droplet morphology dynamically changed in accordance with the concentration gradient of Zonyl. Droplets first passed through a spherical Janus drop morphology before inverting to H/F/W double emulsions (FIG. 5). The reverse was seen when concentrated SDS was added to 0.1% Zonyl-stabilized droplets. These results suggest that not only is droplet morphology highly controllable upon initial emulsification by the choice of surfactants, but that these emulsions may also be dynamically and reversibly reconfigurable by changing the balance of $\gamma_F$ and $\gamma_H$.

Figure 6A:
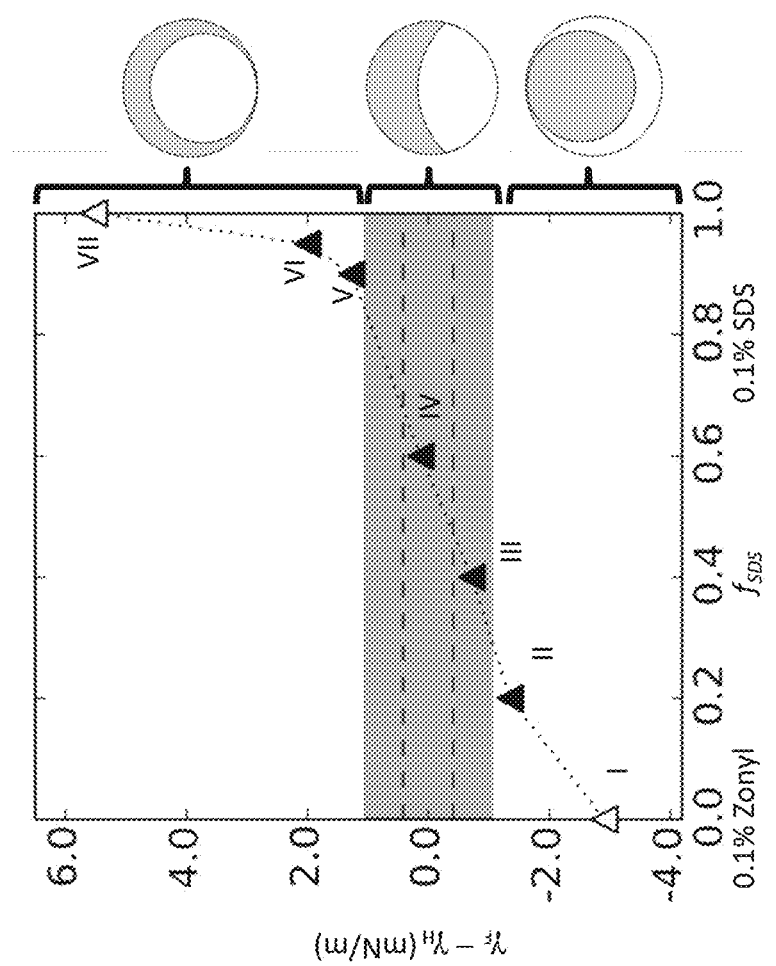
FIG. 6A is a plot of a stability diagram for the hexane-perfluorohexane-water system showing $(\gamma_F - \gamma_H)$ in correlation with the fraction of 0.1% SDS, $f_{SDS}$, where the other fraction is 0.1% Zonyl fluorosurfactant. The grey band denotes the region $|\gamma_F - \gamma_H| < \gamma_{FH} = 1.07 \pm 0.1$ mN/m as obtained from geometrical analysis of Janus droplets. Dashes (---) correspond to $\gamma_{FH} = 0.4$ mN/m at 10° C.
Figure 6B:
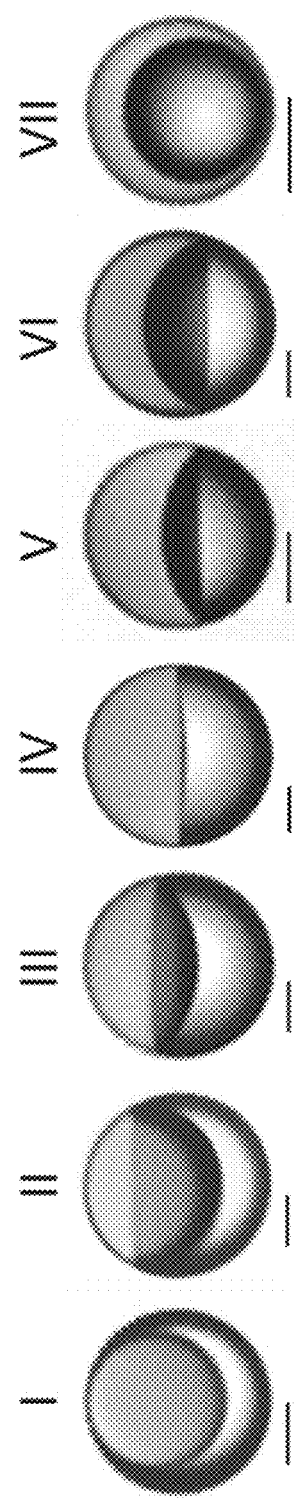
FIG. 6B are optical micrographs of hexane-perfluorohexane droplets in solutions of 0.1% Zonyl and 0.1% SDS in varying ratios as plotted in FIG. 6A. Hexane is dyed and appears grey.
Figure 12:
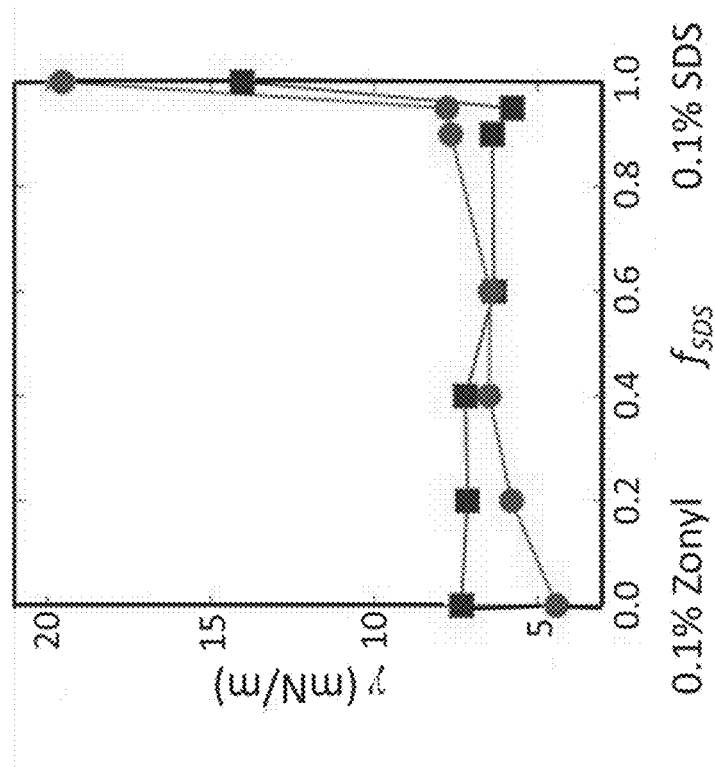
FIG. 12 is a plot of the hexane-water (squares) and perfluorohexane-water (circles) interfacial tensions as a function of fraction of 0.1% SDS, $f_{SDS}$, where the other fraction is 0.1% Zonyl.

To validate the proposed dynamic mechanism and quantify droplet sensitivity, the tensions of hexane-water ($\gamma_H$) and perfluorohexane-water ($\gamma_F$) interfaces under conditions of varying 0.1% SDS and 0.1% Zonyl ratios were determined using the pendant-drop method (FIG. 12). The quantity $\gamma_F - \gamma_H$ can be used as a simple indicator of droplet configuration and this quantity is plotted as a function of surfactant ratio in FIG. 6A. When only 0.1% SDS was used ($f_{SDS}=1$), $\gamma_F - \gamma_H > \gamma_{FH}$ and complete engulfing of perfluorohexane by hexane was observed. In a mixed SDS/Zonyl composition, the trajectory entered the narrow grey zone corresponding to $|\gamma_F - \gamma_H| < \gamma_{FH}$ in FIG. 6A. Within this Janus droplet configurational zone, the droplet morphology began to 'flip' as shown in FIG. 6B. As the proportion of 0.1% SDS approached zero and fluorosurfactant dominated, the trajectory left the Janus zone and the droplets assumed a configuration wherein hexane was encapsulated by perfluorohexane. Overall, the observed droplet geometries demonstrated that hydrocarbon and fluorinated surfactants can be effective for the manipulation of the balance between $\gamma_F$ and $\gamma_H$.

Example 4

The following example describes changing the arrangement of phases of an emulsion in response to a stimulus comprising exposing the emulsion to light.

FIG. 7A illustrates the reversible induction of droplet morphological transitions with stimuli-responsive and/or cleavable surfactants. Responsive surfactants generally display reversible changes in their effectiveness when triggered by stimuli such as magnetic fields, pH, $CO_2$, or light. To create optically responsive droplets, a light-responsive surfactant consisting of an azobenzene moiety that reversibly undergoes a photo-induced isomerization between a more effective trans configuration and a less effective cis configuration was synthesized (FIG. 7B).

Hexanes dyed with Sudan Red 7b and perfluorohexanes in equal volume were used as the component, and an 8:2 ratio of 0.1% light-sensitive surfactant and 0.1% Zonyl FS-300 were used as surfactants in the aqueous phase. A mercury lamp was used as the intense light source, and DAPI and FITC filters were used to selectively allow UV ($\lambda=365$ nm) and blue ($\lambda=470\pm20$ nm) light to reach the sample while imaged on an inverted microscope.

When used in combination with Zonyl, the hexane-perfluorohexane droplets rapidly and reversibly changed morphology in response to UV ($\lambda=365$ nm) and blue ($\lambda=470\pm20$ nm) light. Depending on the relative concentrations of Zonyl and the light-responsive surfactant and/or length of light exposure, the morphology was tuned to switch between the double emulsion and Janus states or to entirely invert (FIG. 7B).

Example 5

The following example describes changing the arrangement of phases of an emulsion in response to a stimulus comprising altering the pH of the emulsion.

Emulsions were formed with Zonyl and a pH-responsive surfactant, N-dodecylpropane-1,3-diamine.

Hexane and perfluorohexane in equal volume were emulsified in a solution of 2 mM N-dodecylpropane-1,3-diamine and 1.2% Zonyl in 0.2 M NaCl. Salt solution was used to control for effects of ionic strength on the emulsion morphology. The pH was adjusted to above and below pH=4.7 by addition of HCl and NaOH.

Figure 8:
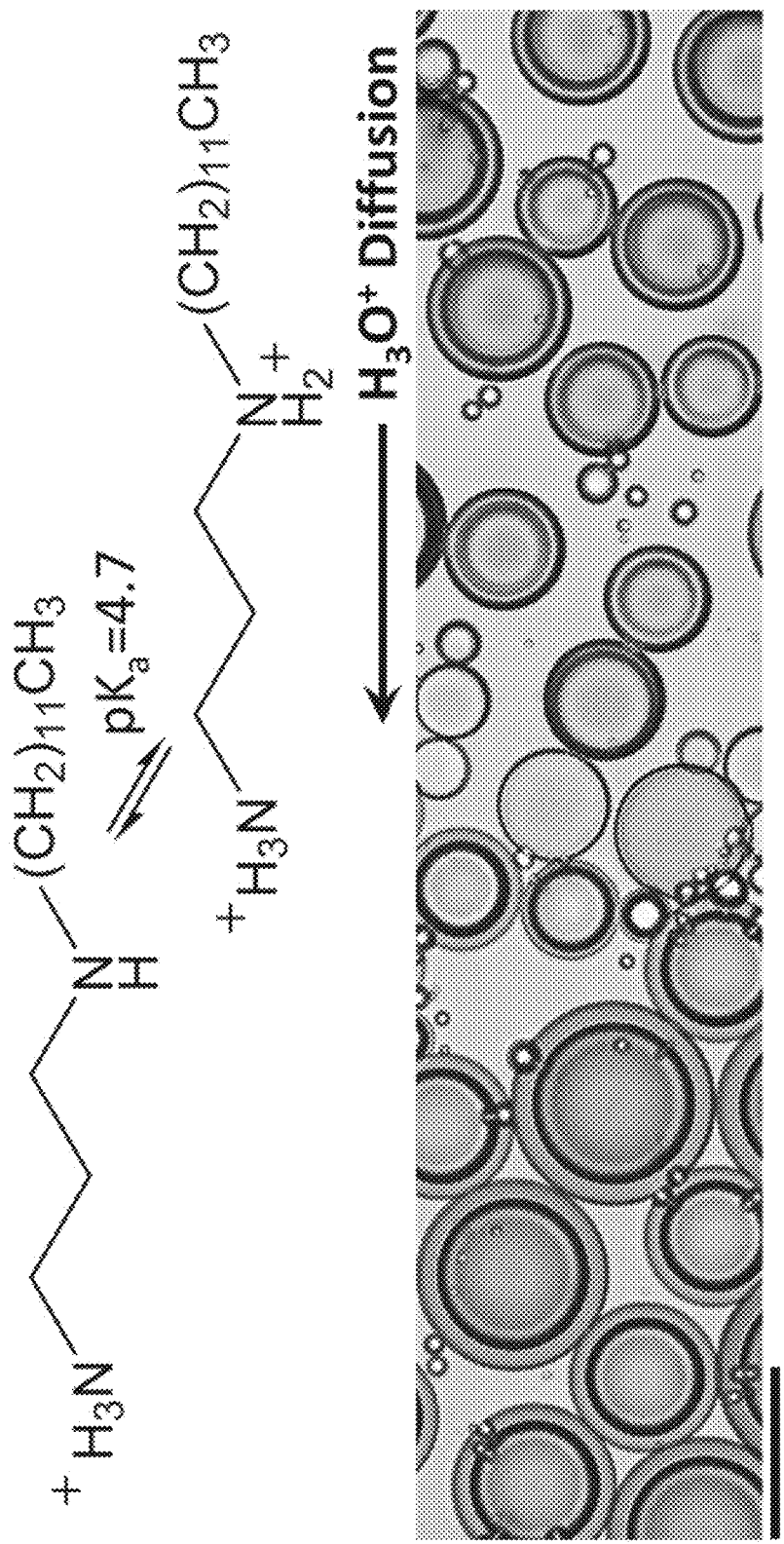
FIG. 8 shows a chemical structure of a pH-responsive surfactant, N-dodecylpropane-1,3-diamine, used in combination with Zonyl to create pH-responsive droplets. Acid diffuses through the solution reducing the pH below pKa=4.7 inducing inversion of the hexane-perfluorohexane emulsions, as shown in the optical micrographs.

Alternating the pH to above and below the surfactant's lowest $pK_a$ value, 4.7 caused rapid and reversible changes in morphology (FIG. 8).

Example 6

The following example describes changing the arrangement of phases of an emulsion in response to a stimulus comprising altering the pH of the emulsion.

Figure 9:
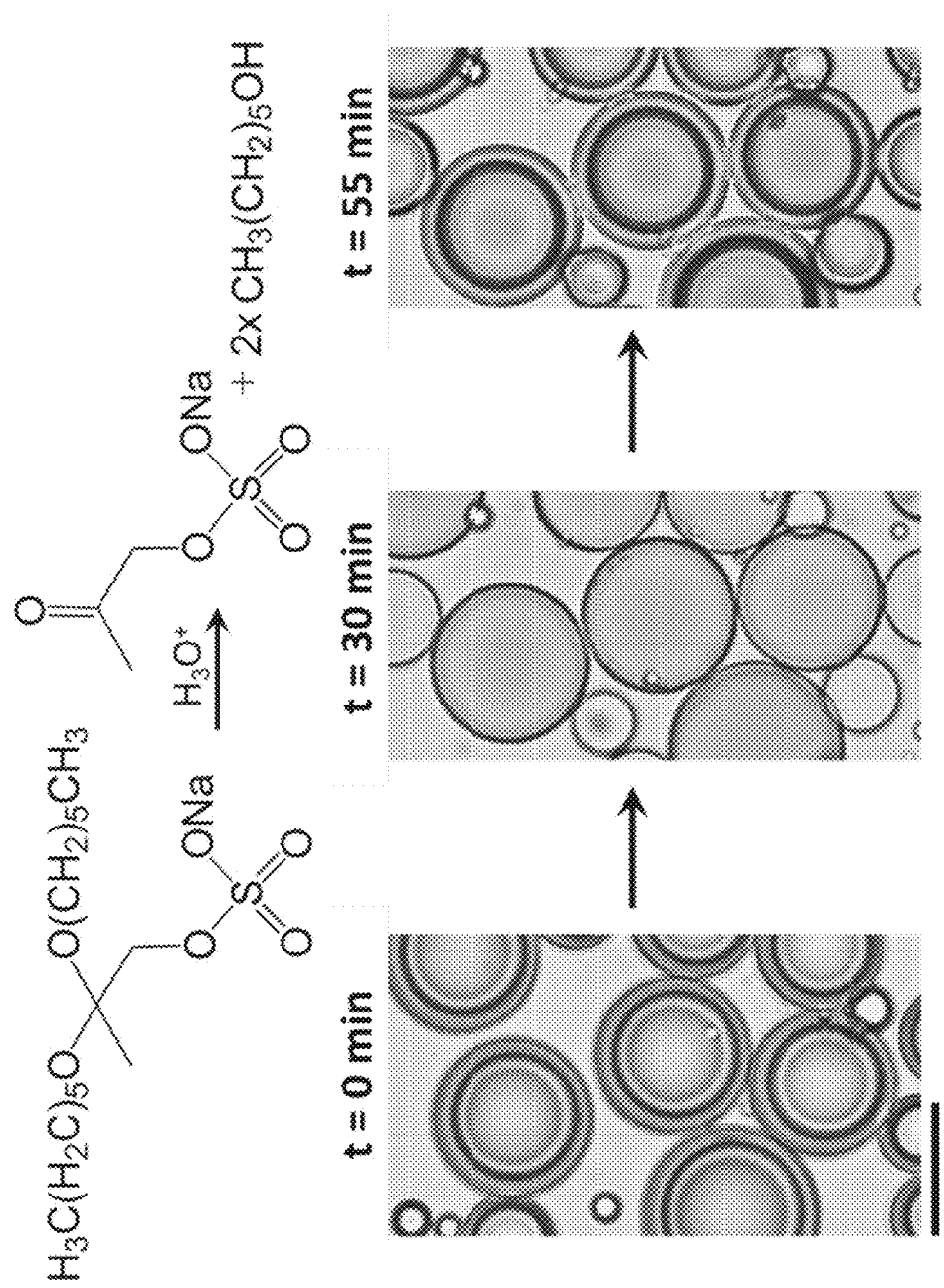
FIG. 9 shows emulsions stabilized by a combination of Zonyl and acid-cleavable surfactant, sodium 2,2-bis(hexyloxy)propyl sulfate, exhibit morphological changes as the cleavable surfactant is degraded over time in pH=3.

Emulsions were formed with a cleavable surfactant. Hexane and perfluorohexane in equal volume were emulsified in a solution of 0.3% sodium 2,2-bis(hexyloxy)propyl sulfate and 0.4% Zonyl in 0.1 M NaCl. The pH was adjusted to 3 using HCl and the solution was allowed to sit undisturbed on the inverted microscope stage while images were periodically taken over an hour. Cleavable surfactants show a reduction in efficacy when irreversibly degraded by exposure to light, heat, or changes in pH. In this context, a irreversible transition between the F/H/W and H/F/W double emulsion states was observed (FIG. 9) using an acid-cleavable surfactant, sodium 2,2-bis(hexyloxy)propyl sulfate, in conjunction with Zonyl. The results shown here demonstrate the versatility of the complex fluorous-hydrocarbon droplets' response towards a wide range of stimuli.

Example 7

The following example describes the formation of an emulsion comprising Janus droplets.

Figure 10A:
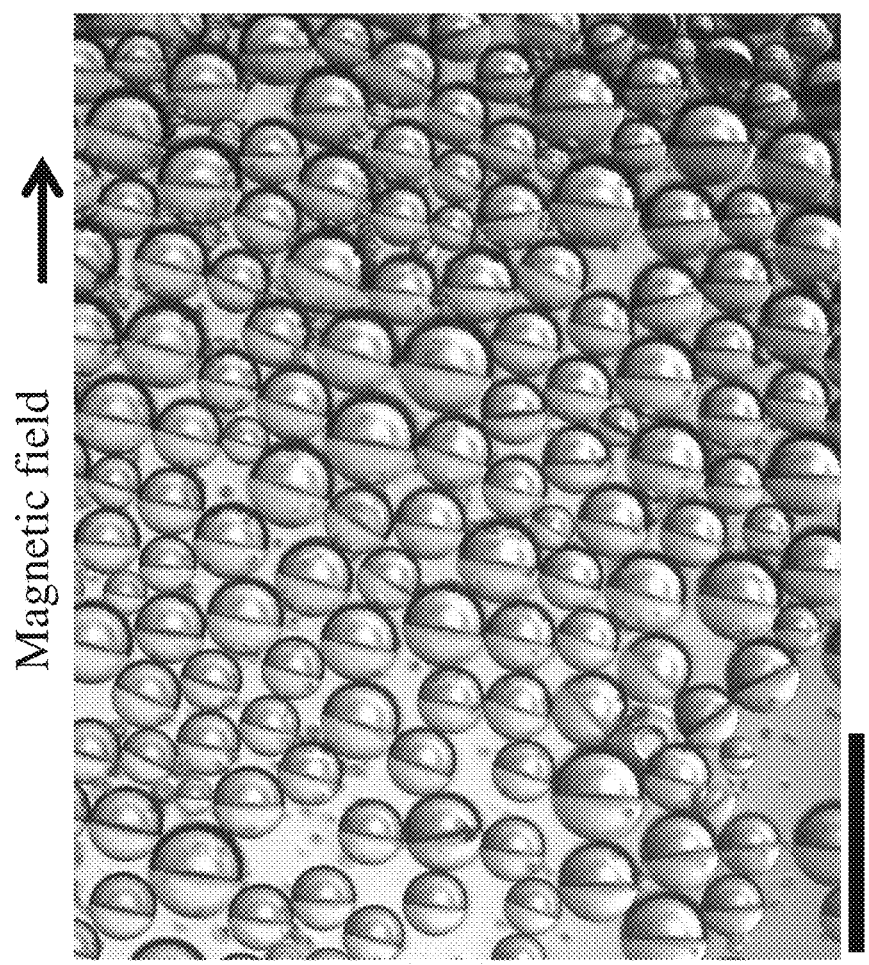
FIG. 10A shows an optical micrograph of Janus droplets, formed according to one set of embodiments.

Liquid droplets and solid droplets with asymmetric properties were created by affecting different chemistries in the separate compartments of a fluorous-hydrocarbon Janus droplet. To create directionally-orientable and movable liquid Janus droplets, magnetic $Fe_3O_4$ nanoparticles stabilized with oleic acid were synthesized for preferential partitioning into the hydrocarbon phase. Magnetite nanoparticles were made as follows: 25 mL of concentrated $NH_3OH$ was added to an acidified solution of 1.6 g of $FeCl_3$ and 1 g of $FeCl_2.4H_2O$ in 50 mL of water at 80° C. The magnetite nanoparticle precipitate was collected with a magnet, washed with water, and redispersed. 1 g of sodium oleate in 10 mL of water was added under stirring at room temperature. The oily black precipitate was extracted with hexanes. Solid was collected by evaporation of solvent and subsequently redispersed in dichlorobenzene. Janus droplets were obtained by heating the nanoparticle/dichlorobenzene solution and ethyl nonafluorobutyl ether above the Tc and shaking in 0.2% SDS and 0.2% Zonyl in a 2.5:1 ratio. The droplets were oriented using a neodymium magnet. Upon inclusion in a Janus emulsion of dichlorobenzene and ethyl nonafluorobutyl ether, the nanoparticle/dichlorobenzene hemispheres rapidly oriented and moved in the direction of a magnet (FIG. 10A).

Figure 10B:
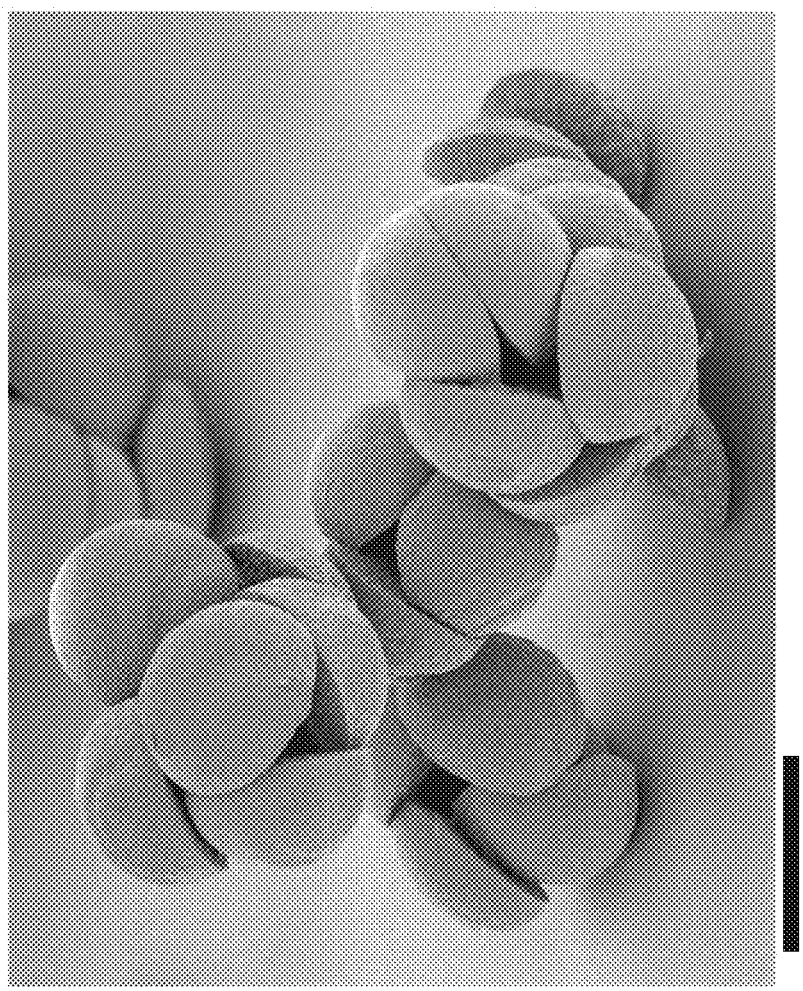
FIG. 10B shows a scanning electron micrograph of particles formed from polymerized Janus droplets, formed according to one set of embodiments.
Figure 10C:
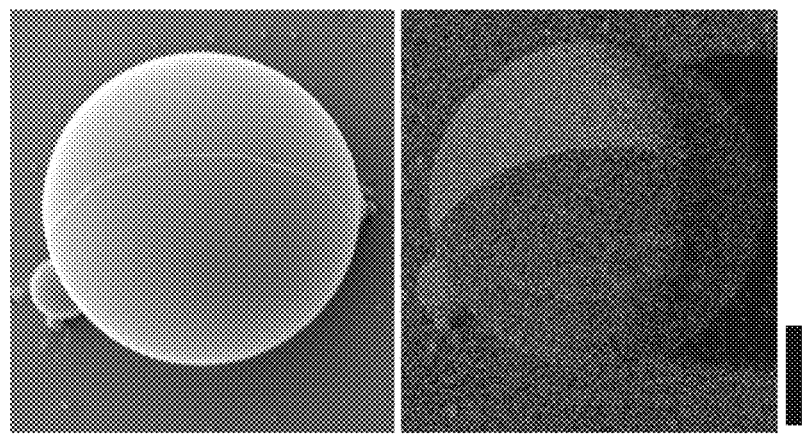
FIG. 10C shows a scanning electron micrograph (top) and an energy dispersive x-ray map highlighting fluorine (bottom) of a Janus droplet, formed according to one set of embodiments.

To generate solid hemispherical droplets, an emulsion consisting of a liquid polymer precursor, 1,6-hexanediol diacrylate, as the hydrocarbon phase and methoxyperfluorobutane as the fluorous phase, was polymerized (FIG. 10B). 1-6, hexanediol diacrylate with 4% Darocur 1173 photoinitiator was heated with equal volume methoxyperfluorobutane above the Tc and emulsified. 1% SDS and 1% Zonyl in a 3:2 ratio yielded Janus droplets which were then polymerized under a UV lamp while kept cold on ice. By replacing methoxyperfluorobutane with a fluorinated acrylate oligomer and crosslinker (e.g., 2,2,3,3,4,4,5,5,6,6,7,7,8,8,9,9-hexadecafluorodecane-1,10-diylbis(2-methylacrylate)), spherical solid Janus droplets with fluorinated and non-fluorinated sides were created (FIG. 10C).

Example 8

Figure 11:
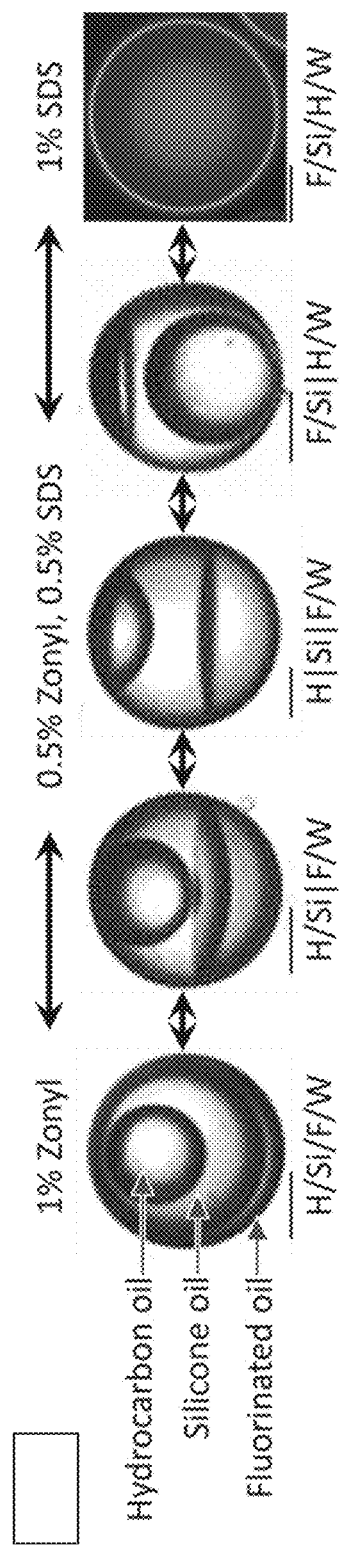
FIG. 11 shows optical micrographs of four-phase emulsions reconfiguring in response to changes in interfacial tension. Droplets contain hydrocarbon oil (H, mineral oil with octadecane), silicone oil (Si), and fluorinated oil (F, ethyl nonafluorobutyl ether) emulsified in water (W). The silicone phase is enriched with a fraction of the two other phases. Left: 1% Zonyl generates a H/Si/F/W triple emulsion. Right: 1% SDS generates a F/Si/H/W triple emulsion with a thin outer shell. Phases were identified with fluorescent dyes.

The same principles of droplet transformations observed in three-phase emulsions, and described in Example 1, were extended to a four-phase system thereby generating reconfigurable droplets of even higher order complexity. A system comprising of silicone oil (Si), hydrocarbon oil (H, mineral oil and octadecane), and fluorinated oil (F, ethyl nonafluorobutyl ether) was designed such that the liquids mixed with heating and separated into three phases at room temperature (FIG. 11). Light mineral oil with 20 wt % octadecane (used to reduce the $T_c$ in a mixture with the other liquids), silicone oil, and ethyl nonafluorobutyl ether were used as the components in a volume ratio of 6:7:13. The mineral oil and ethyl nonafluorobutyl ether both partitioned into the silicone oil such that upon phase separation, the silicone oil phase is enriched with some quantity of the two other phases. Aqueous mixtures of varying ratios of 1% Zonyl and 1% SDS were used as the outer phase, and emulsions were formed in the bulk by shaking.

Systematically varying ratios of 1% Zonyl and 1% SDS aqueous surfactant solutions caused droplets to assume morphologies combining both Janus configurations (denoted as "|") and encapsulated configurations (denoted as "/") (FIG. 11). For example, a triple emulsion H/Si/F/W was formed in 1% Zonyl, but at a 3:2 ratio of 1% Zonyl:1% SDS, formed a Janus configuration between the fluorous and silicone phases while the hydrocarbon phase remained encapsulated in the silicone phase, H/Si|F/W. As the ratio of SDS increased, the droplet passed through Janus droplet and mixed Janus-encapsulated droplet configurations before inverting to the reverse triple emulsion (F/Si/H/W) in 1% SDS.

Example 9

The following example demonstrates the sensing of an analyte using an emulsion.

For all samples, measurements of transmission at 650 nm through a thin film of droplets were taken over time. A stabilized tungsten halogen lamp served as the light source and the transmitted light was collected with an optical fiber fitted with a collimating lens. The transmission measurements were quantified using a USB spectrometer and computer software (Ocean Optics). Zonyl® FS-300 (40% solids in water) was purchased from Sigma-Aldrich. Perfluorohexane, mixture of isomers, was purchased from SynQuest. The enzymes used, α-amylase from *Aspergillus oryzae* and lipase from *Candida* sp. were purchased from Sigma-Aldrich. Triton X-100 was purchased from Sigma-Aldrich, γ-cyclodextrin was purchased from TCI, and FC-770 is a product of 3M™.

Amylase Sensing Experiments

Figure 13A:
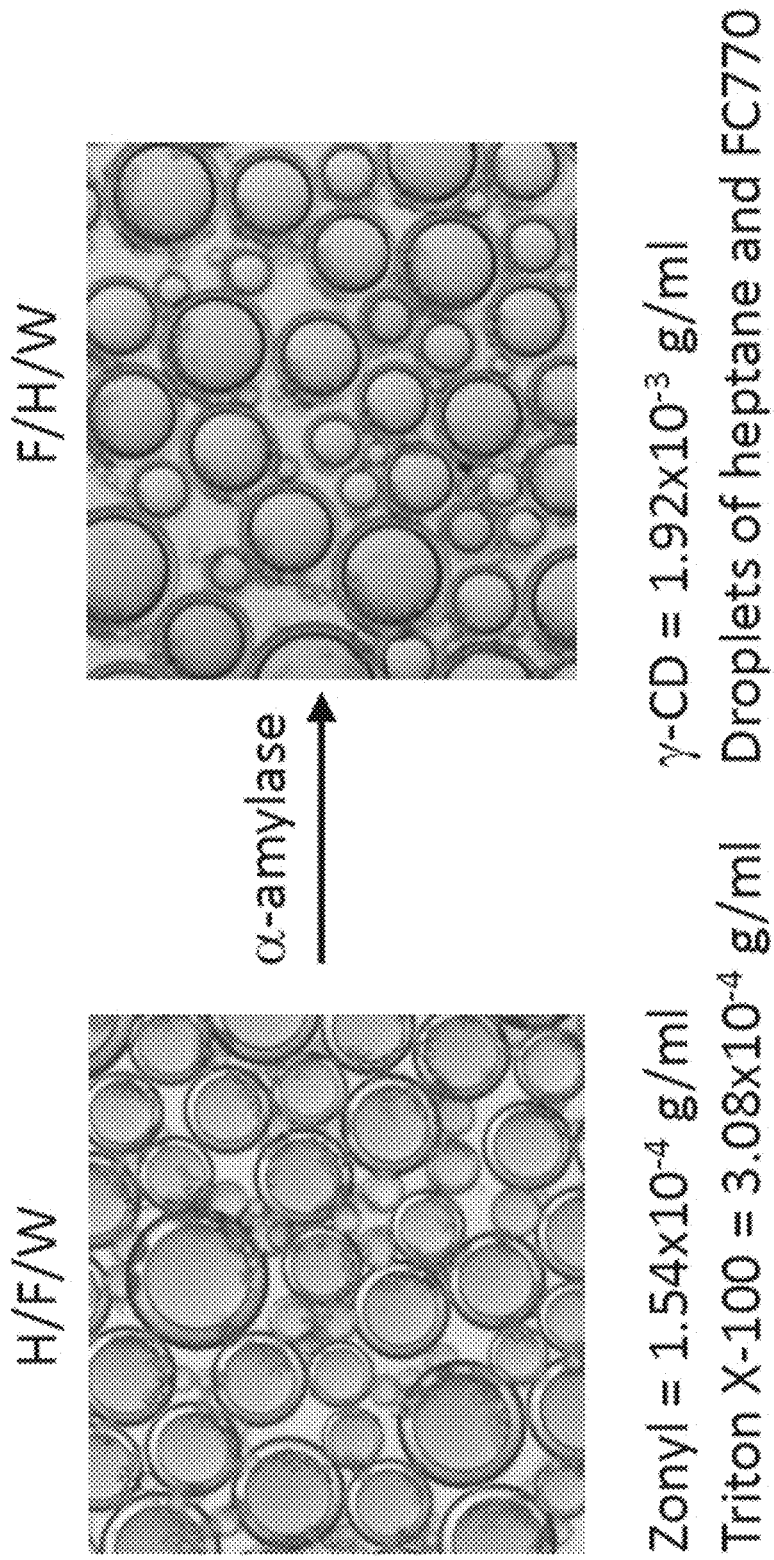
FIG. 13A shows images of the reversal of the arrangement of the complex droplets in the presence of α-amylase.

The complex droplets consisted of heptane and FC770 fluorocarbon (from 3M™) in a 1:1 volume ratio. The heptane-FC770 and the outer aqueous phase (20 microliters of 1 wt % Zonyl® FS-300 in 978 microliters of sodium acetate buffer, 0.2M, pH 5.2) were heated above the critical temperature, 35 microliters of the miscible heptane-FC770 were added to the aqueous outer phase, and the solution was emulsified using a vortex mixer. Subsequently after droplet formation, 40 microliters of 1 wt % Triton X-100 in sodium acetate buffer and 250 microliters of 1 wt % γ-cyclodextrin in sodium acetate buffer were slowly added. The complex emulsion was warmed in an incubator at 37° C. 18 microliters of amylase of varying concentrations in sodium acetate buffer were added, the complex emulsion was poured into the sample holder, and the transmission measurements were taken over time at 37° C.

γ-cyclodextrin generally binds to Triton X-100 and reduces the relative effectiveness of the surfactant. α-amylase is known to generally degrade γ-cyclodextrin. FIG. 13A shows the reversal of the arrangement of the complex droplets in the presence of α-amylase as the α-amylase degrades the γ-cyclodextrin bound to the Trition X-100, changing the miscibility of the surfactant and resulting in a rearrangement of the complex droplet components.

Figure 13B:
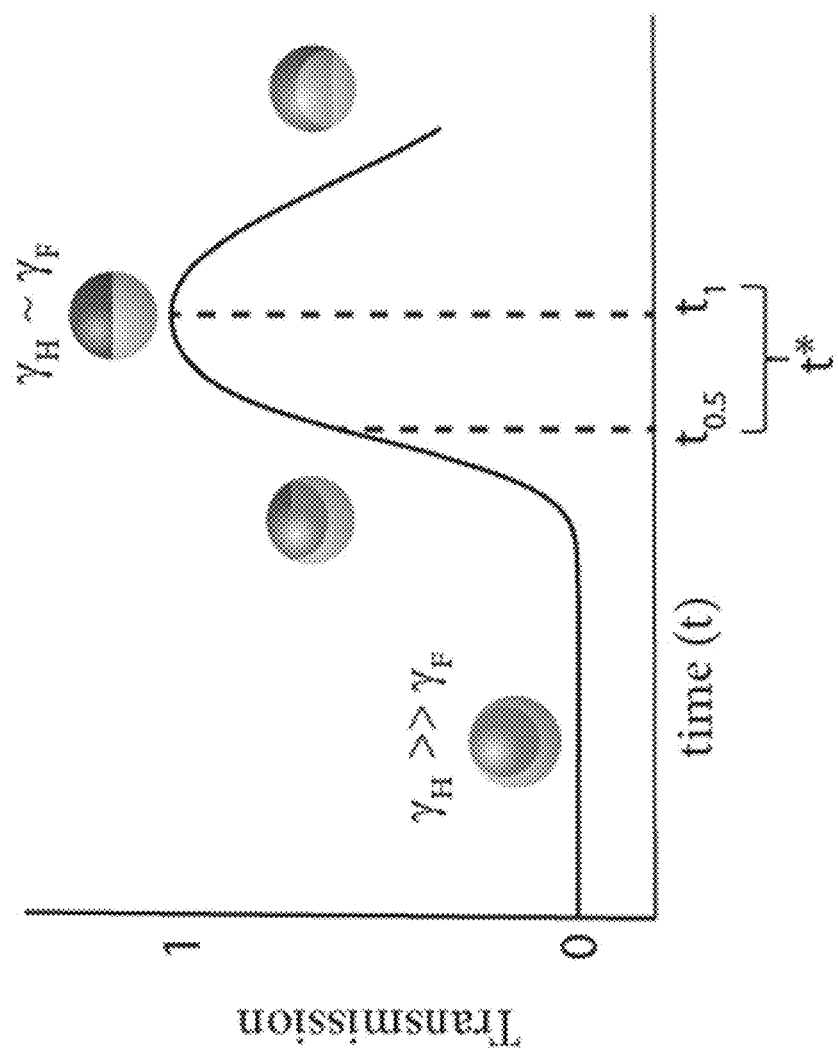
FIG. 13B illustrates the determination of time constant, t*, for the change in optical transmission of the complex droplet, according to some embodiments.
Figure 13C:
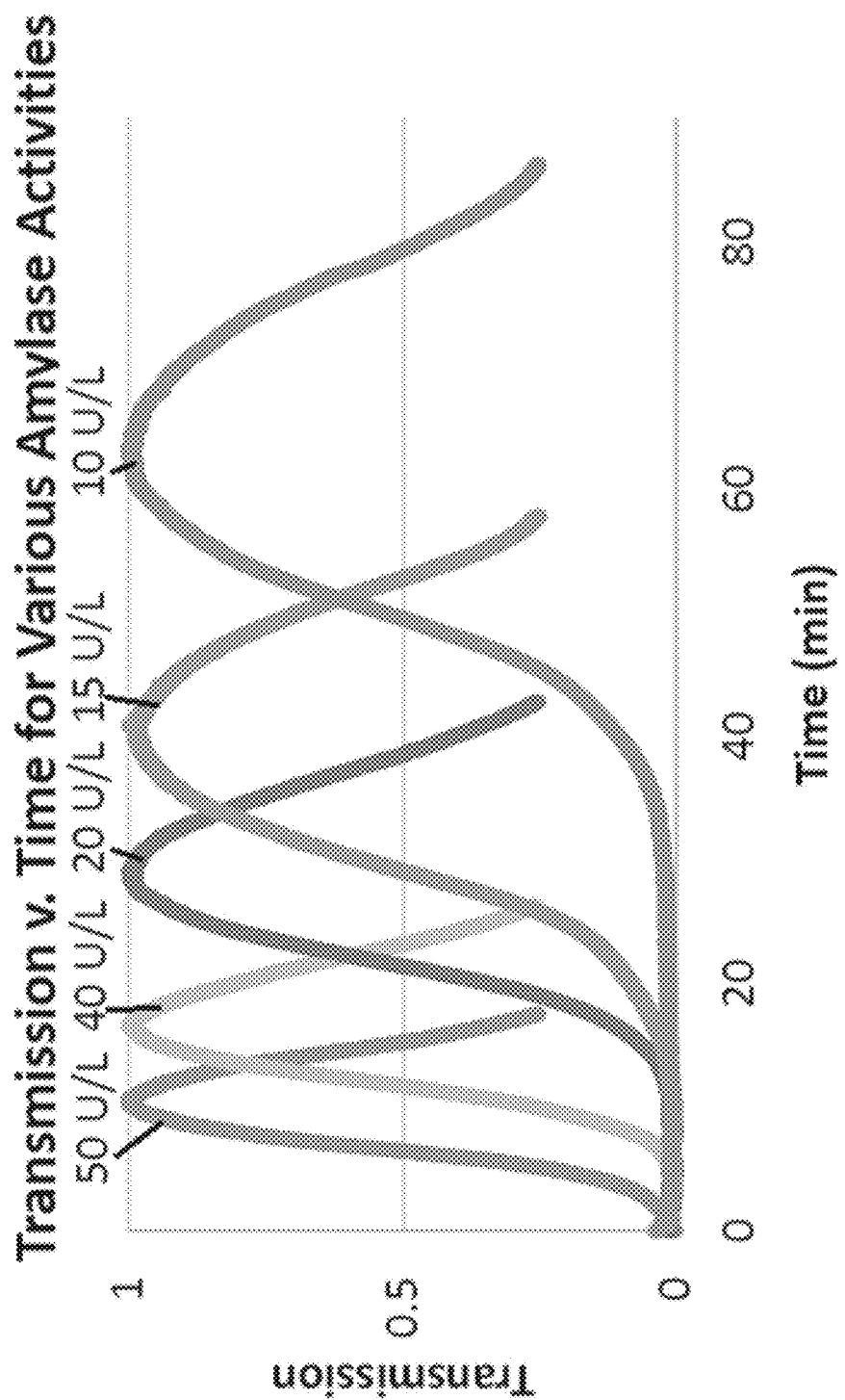
FIG. 13C shows the transmission of a colloid versus time for various activities of α-amylase added to the colloid, according to some embodiments.
Figure 13D:
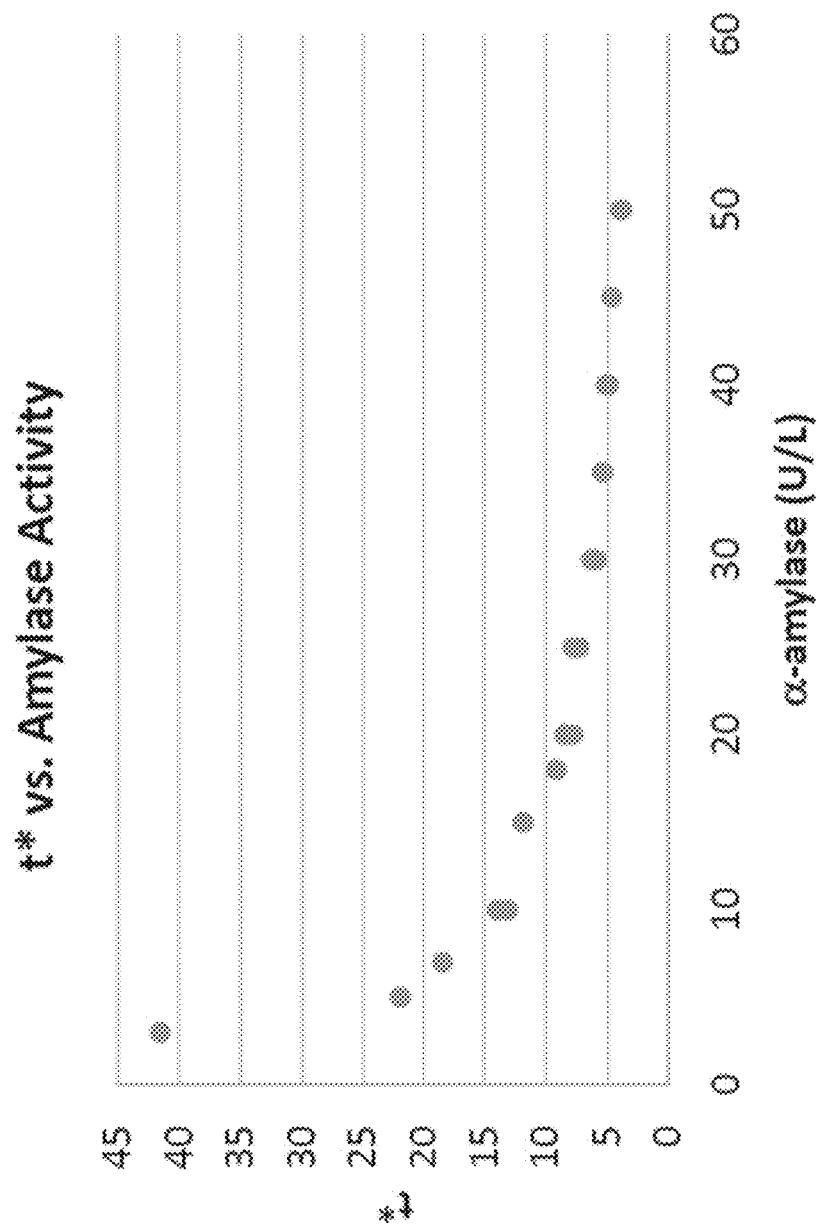
FIG. 13D shows a plot of t* versus α-amylase activity for a colloid, according to some embodiments.

FIG. 13B illustrates the determination of time constant, t*, for the change in optical transmission of the complex droplet. FIG. 13C shows the transmission versus time for various activities of α-amylase and FIG. 13D shows a plot of t* versus α-amylase activity.

The time constant, t*, is defined as the time elapsed between the time of maximum transmission and the time that half the maximum transmission is reached (transmission=0.5), where the transmission is normalized such that minimum transmission is defined as transmission=0 and the maximum is defined as transmission=1.

Lipase Sensing Experiments

The complex droplets consisted of perfluorohexane and a mixture of (2:1 volume ratio hexane:heptane) in a 1:1 volume ratio. The hydrocarbon-fluorocarbon mixture and the outer aqueous phase (20 microliters of 1 wt % Zonyl® FS-300 in 992 microliters 1× phosphate buffered saline, pH 7.6) were heated above the critical temperature, 50 microliters of the miscible hydrocarbon-fluorocarbon pair were added to the outer aqueous outer phase, and the solution was emulsified using a vortex mixer. After emulsification, 270 microliters of 1 vol % tetra(ethylene glycol)mono-n-octanoate in in PBS were slowly added. 12 microliters of lipase of varying concentrations in PBS were added, the complex emulsion was poured into the sample holder, and transmission measurements were taken over time at room temperature (20-21° C.).

Figure 14A:
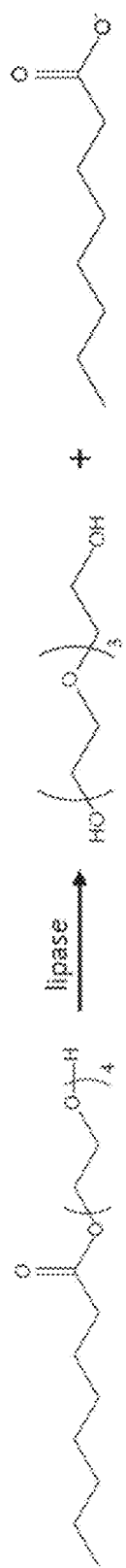
FIG. 14A shows the degradation of tetra(ethylene glycol) mono-n-octanoate in the present of lipase.
Figure 14B:
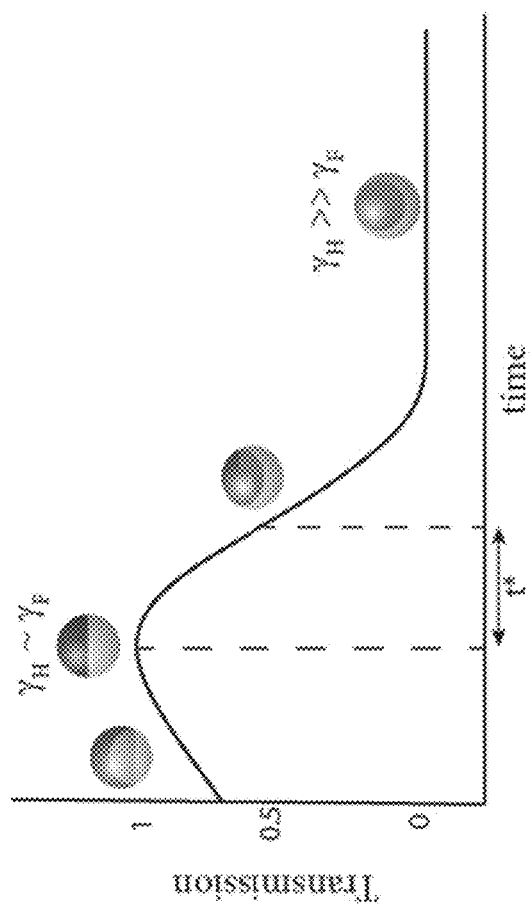
FIG. 14B shows the change in transmission of an emulsion film containing a plurality of complex droplets in the presence of lipase over time.
Figure 14B:
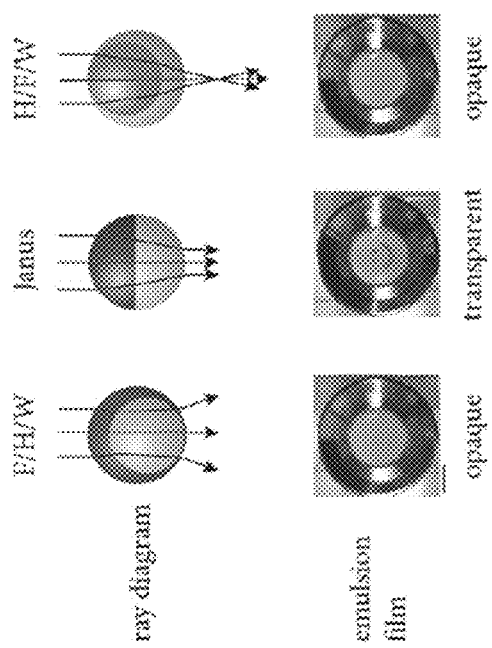
Figure 14C:
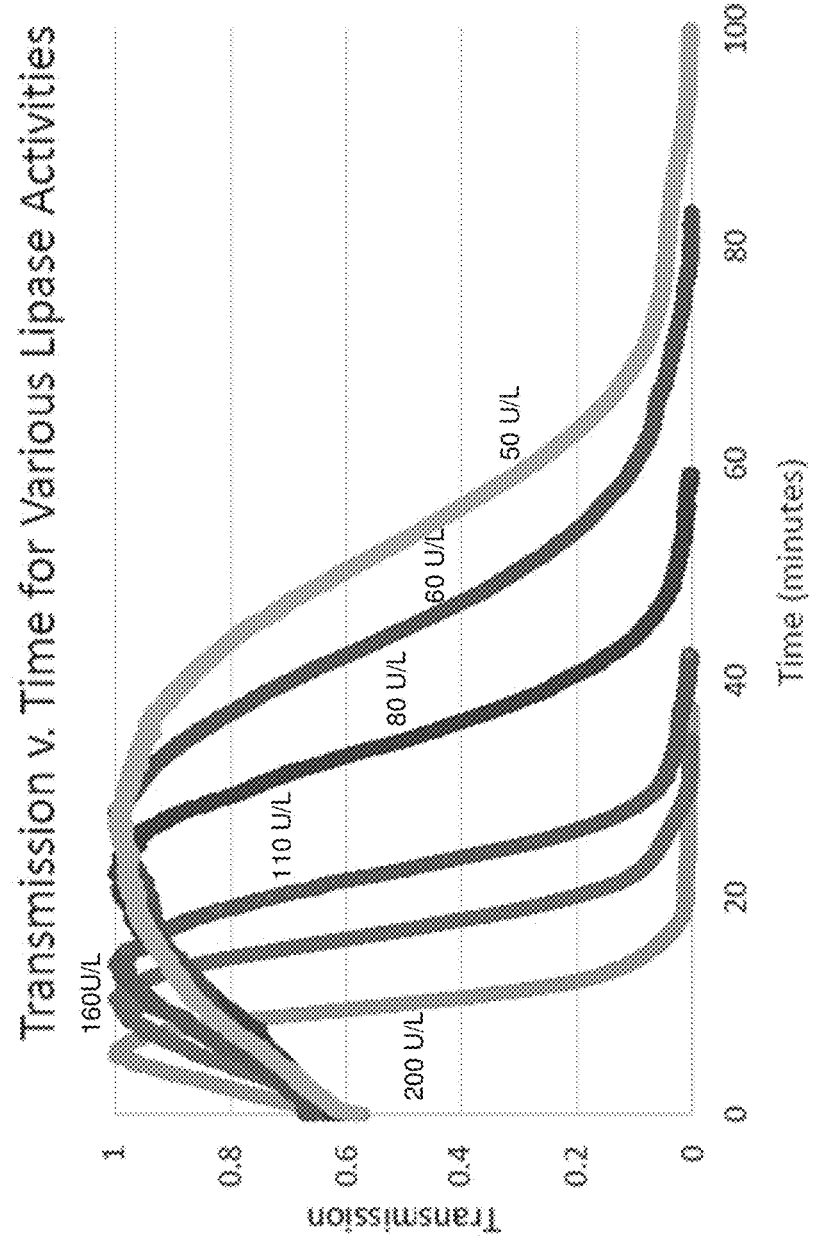
FIG. 14C shows the transmission versus time for various activities of lipase.
Figure 14D:
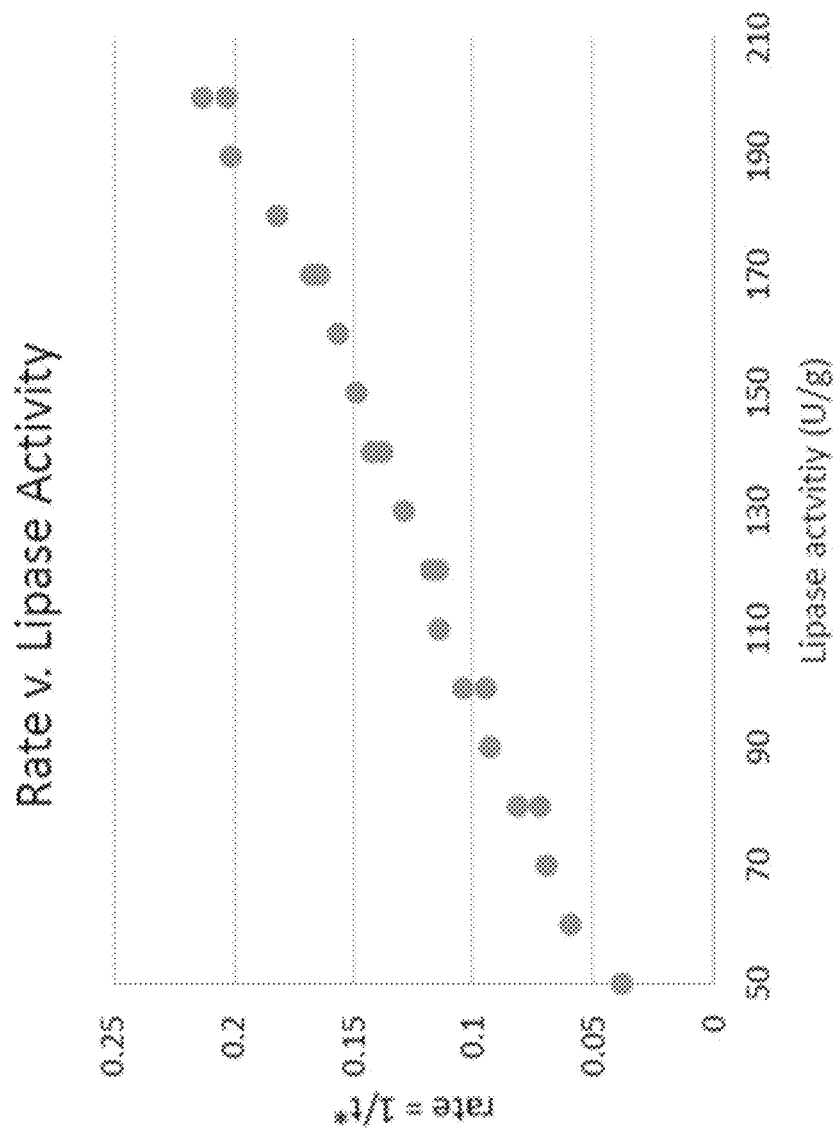
FIG. 14D shows a plot of (1/t*) versus lipase activity for a colloid, according to some embodiments.

FIG. 14A shows the degradation of tetra(ethylene glycol) mono-n-octanoate in the present of lipase. FIG. 14B shows the change in transmission of an emulsion film containing a plurality of complex droplets in the presence of lipase over time. FIG. 14C shows the transmission versus time for various activities of lipase and FIG. 14D shows a plot of (1/t*) versus lipase activity.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A method of changing the arrangement of droplet phases, comprising:
   providing a colloid comprising:
      an outer phase; and
      a plurality of droplets dispersed within the outer phase, wherein at least a portion of the plurality of droplets comprise a first component and a second component, the first component immiscible with the second component; and
   stimulating the colloid, such that the first component and the second component change arrangement and such that the first component and the second component are immiscible with each other after changing arrangement.

2. The method of claim 1, wherein the method comprises stimulating the colloid such that the first component and the second component transpose.

3. The method of claim 1, wherein the method comprises stimulating the colloid such that a portion of the plurality of droplets form a Janus droplet comprising the first component and the second component.

4. The method of claim 1, wherein stimulating the colloid comprises exposing the colloid to electromagnetic radiation, ionizing radiation, a magnetic field, an electric field, a mechanical force, or combinations thereof.

5. The method of claim 1, wherein stimulating the colloid comprises adjusting the ionic strength of the colloid.

6. The method of claim 1, wherein stimulating the colloid comprises adjusting the temperature of the colloid.

7. The method of claim 1, wherein stimulating the colloid comprises exposing the colloid to photochemical stimulation.

8. The method of claim 1, wherein stimulating the colloid comprises adding an analyte to the colloid.

9. The method of claim 8, wherein the analyte comprises a biological compound, a drug, a macromolecule, a salt, an electrolyte, an enzyme, a nucleic acid, a carbohydrate, a peptide, a protein, a lipid, a phosphate, a sulfonate, a virus, a pathogen, an oxidant, a reductant, a toxin, a chemical warfare agent, an explosive, carbon dioxide, or combinations thereof.

10. The method of claim 8, wherein the analyte comprises a surfactant.

11. The method of claim 1, wherein the method comprises stimulating the colloid such at least one of the components changes conformation.

12. The method of claim 1, wherein the method comprises stimulating the colloid such that the colloid releases at least one of the components.

13. The method of claim 1, wherein the method comprises stimulating the colloid such that an average birefringence of the colloid changes.

14. The method of claim 1, wherein the method comprises stimulating the colloid such that an average optical transmission of the colloid changes.

15. The method of claim 1, wherein the method comprises stimulating the colloid such that a color of the colloid changes.

16. The method of claim 1, wherein the method comprises stimulating the colloid such that an average luminescence of the colloid changes.

17. The method of claim 1, wherein the first component and the second component are immiscible with one another before stimulating the colloid.

18. The method of claim 1, wherein upon stimulating the colloid the first component and the second component become miscible with one another.

19. The method of claim 1, wherein the method comprises, after the first component and the second component change arrangement, the first component and the second component are immiscible with one another.

20. The method of claim 1, wherein the first component and the second component change arrangement reversibly.

21. A method of changing the arrangement of droplet phases, comprising:
   providing a colloid comprising:
      an outer phase; and
      a plurality of droplets dispersed within the outer phase, wherein at least a portion of the plurality of droplets a first component and a second component, the first component immiscible with the second component; and
   stimulating the colloid, such that the first component and the second component become miscible with each other; and
   further stimulating the colloid, such that the first component and the second component become immiscible with each other.

22. A method of changing the arrangement of droplet phases, comprising:
   providing a colloid comprising:
      an outer phase; and
      a plurality of droplets dispersed within the outer phase, wherein at least a portion of the plurality of droplets comprises a first component at least partially encapsulated by a second component immiscible with the first component; and
   stimulating the colloid, such that the second component becomes at least partially encapsulated by the first component.

* * * * *